(12) United States Patent
Bansal

(10) Patent No.: US 10,131,706 B2
(45) Date of Patent: *Nov. 20, 2018

(54) ANTI-FACTOR BB ANTIBODIES

(71) Applicant: NovelMed Therapeutics, Inc., Cleveland, OH (US)

(72) Inventor: Rekha Bansal, Cleveland, OH (US)

(73) Assignee: NOVELMED THERAPEUTICS, INC., Cleveland, OH (US)

(*) Notice: Subject to any disclaimer, the term of this patent is extended or adjusted under 35 U.S.C. 154(b) by 465 days.

This patent is subject to a terminal disclaimer.

(21) Appl. No.: 14/659,098

(22) Filed: Mar. 16, 2015

(65) Prior Publication Data

US 2016/0002348 A1 Jan. 7, 2016

Related U.S. Application Data

(63) Continuation-in-part of application No. 12/675,220, filed as application No. PCT/US2008/074489 on Aug. 27, 2008, now Pat. No. 8,981,060.

(60) Provisional application No. 60/968,146, filed on Aug. 27, 2007.

(51) Int. Cl.
C07K 16/40 (2006.01)
A61K 39/395 (2006.01)
C07K 16/18 (2006.01)

(52) U.S. Cl.
CPC .......... *C07K 16/18* (2013.01); *C07K 2317/14* (2013.01); *C07K 2317/76* (2013.01); *C07K 2317/92* (2013.01)

(58) Field of Classification Search
None
See application file for complete search history.

(56) References Cited

U.S. PATENT DOCUMENTS 8,981,060 B2 * 3/2015 Bansal .................. C07K 16/18
424/130.1
2005/0107319 A1 5/2005 Bansal

FOREIGN PATENT DOCUMENTS

WO 99/10009 A1 3/1999
WO 2007/056227 A1 5/2007

OTHER PUBLICATIONS

Uwai, Masaya, et al. "A New Apoptotic Pathway for the Complement Factor B-Derived Fragment Bb", Journal of Cellular Physiology 185:280-292 (2000).
Ueda et al., "probing functional sites on complement protein B with monoclonal antibodies" J. Immunology, 138, (1987), pp. 1143-1149.
Holers et al., "The alternative pathway of complement in disease: opportunities for therapeutic targeting" Molecular Immunology, 41 (2004), pp. 147-152.
Cornacoff et al., "Primate erythrocyte-immune complex-clearing mechanism" J. Clin. Invest. 71, 1983, pp. 236-247. V.
Ponnuraj et al. "Structural analysis of engineered Bb fragmetn of complement factor B: insights into the activation mechanism of the alternative pathway C3-convertase" Molecular Cell, 14, 17-28, Apr. 9, 2004.
Thurman, Joshua, M., et al., "The Central Role of the Alternative Complement Pathway in Human Disease", The Journal of Immunology, 2006, vol. 176, 1305-1310.

* cited by examiner

Primary Examiner — Phillip Gambel
(74) Attorney, Agent, or Firm — Tarolli, Sundheim, Covell & Tummino LLP

(57) ABSTRACT

A pharmaceutical composition includes an isolated anti-Bb antibody or antigen binding portion thereof produced by a hybridoma cell line deposited under ATCC Accession Number PTA-8543 or an isolated anti-Bb antibody or antigen binding portion thereof that competitively inhibits binding of the antibody or antigen binding portion produced by the hybridoma cell line deposited under ATCC Accession Number PTA-8543 to the Bb segment of factor B; and a pharmaceutically acceptable carrier.

12 Claims, 37 Drawing Sheets

Specification includes a Sequence Listing.

The Antibody of this invention is a Specific Inhibitor of C3 Convertase

Antibodies of Prior Art Prevent Factor B Binding to C3b

SDS-PAGE of 1D3 Monoclonal Antibody

Lane 1: 1D3
Lane 2: Molecular weight marker

**Biotinlyated Anti-Bb Binding to Bb
is Inhibited by Anti-Bb**

Detect Neut. HRP
Biot NM001
Cold NM001
$IC_{50} = 9.5 \pm 1$ nM
$IC_{95} = \sim 186$ nM

Fig. 37

Biotinlyated Anti-Bb Binding to Bb is not Inhibited by Another Anti-Bb Antibody (NM1209)

Fig. 38

SEQUENCE LISTING

```
<160> NUMBER OF SEQ ID NOS: 6

<210> SEQ ID NO 1
```

-continued

```
<211> LENGTH: 739
<212> TYPE: PRT
<213> ORGANISM: Homo sapiens

<400> SEQUENCE: 1

Thr Pro Trp Ser Leu Ala Trp Pro Gln Gly Ser Cys Ser Leu Glu Gly
1               5                   10                  15

Val Glu Ile Lys Gly Gly Ser Phe Arg Leu Gln Glu Gly Gln Ala
            20                  25                  30

Leu Glu Tyr Val Cys Pro Ser Gly Phe Tyr Pro Tyr Pro Val Gln Thr
            35                  40                  45

Arg Thr Cys Arg Ser Thr Gly Ser Trp Ser Thr Leu Lys Thr Gln Asp
    50                  55                  60

Gln Lys Thr Val Arg Lys Ala Glu Cys Arg Ala Ile His Cys Pro Arg
65                  70                  75                  80

Pro His Asp Phe Glu Asn Gly Glu Tyr Trp Pro Arg Ser Pro Tyr Tyr
                85                  90                  95

Asn Val Ser Asp Glu Ile Ser Phe His Cys Tyr Asp Gly Tyr Thr Leu
            100                 105                 110

Arg Gly Ser Ala Asn Arg Thr Cys Gln Val Asn Gly Arg Trp Ser Gly
        115                 120                 125

Gln Thr Ala Ile Cys Asp Asn Gly Ala Gly Tyr Cys Ser Asn Pro Gly
    130                 135                 140

Ile Pro Ile Gly Thr Arg Lys Val Gly Ser Gln Tyr Arg Leu Glu Asp
145                 150                 155                 160

Ser Val Thr Tyr His Cys Ser Arg Gly Leu Thr Leu Arg Gly Ser Gln
                165                 170                 175

Arg Arg Thr Cys Gln Glu Gly Gly Ser Trp Ser Gly Thr Glu Pro Ser
            180                 185                 190

Cys Gln Asp Ser Phe Met Tyr Asp Thr Pro Gln Glu Val Ala Glu Ala
        195                 200                 205

Phe Leu Ser Ser Leu Thr Glu Thr Ile Glu Gly Val Asp Ala Glu Asp
    210                 215                 220

Gly His Gly Pro Gly Glu Gln Gln Lys Arg Lys Ile Val Leu Asp Pro
225                 230                 235                 240

Ser Gly Ser Met Asn Ile Tyr Leu Val Leu Asp Gly Ser Asp Ser Ile
                245                 250                 255

Gly Ala Ser Asn Phe Thr Gly Ala Lys Lys Cys Leu Val Asn Leu Ile
            260                 265                 270

Glu Lys Val Ala Ser Tyr Gly Val Lys Pro Arg Tyr Gly Leu Val Thr
        275                 280                 285

Tyr Ala Thr Tyr Pro Lys Ile Trp Val Lys Val Ser Glu Ala Asp Ser
    290                 295                 300

Ser Asn Ala Asp Trp Val Thr Lys Gln Leu Asn Glu Ile Asn Tyr Glu
305                 310                 315                 320

Asp His Lys Leu Lys Ser Gly Thr Asn Thr Lys Lys Ala Leu Gln Ala
                325                 330                 335

Val Tyr Ser Met Met Ser Trp Pro Asp Asp Val Pro Pro Glu Gly Trp
            340                 345                 350

Asn Arg Thr Arg His Val Ile Ile Leu Met Thr Asp Gly Leu His Asn
        355                 360                 365

Met Gly Gly Asp Pro Ile Thr Val Ile Asp Glu Ile Arg Asp Leu Leu
    370                 375                 380

Tyr Ile Gly Lys Asp Arg Lys Asn Pro Arg Glu Asp Tyr Leu Asp Val
```

```
                385                 390                 395                 400
        Tyr Val Phe Gly Val Gly Pro Leu Val Asn Gln Val Asn Ile Asn Ala
                        405                 410                 415

Leu Ala Ser Lys Lys Asp Asn Glu Gln His Val Phe Lys Val Lys Asp
                        420                 425                 430

Met Glu Asn Leu Glu Asp Val Phe Tyr Gln Met Ile Asp Glu Ser Gln
                        435                 440                 445

Ser Leu Ser Leu Cys Gly Met Val Trp Glu His Arg Lys Gly Thr Asp
                450                 455                 460

Tyr His Lys Gln Pro Trp Gln Ala Lys Ile Ser Val Ile Arg Pro Ser
        465                 470                 475                 480

Lys Gly His Glu Ser Cys Met Gly Ala Val Val Ser Glu Tyr Phe Val
                        485                 490                 495

Leu Thr Ala Ala His Cys Phe Thr Val Asp Asp Lys Glu His Ser Ile
                        500                 505                 510

Lys Val Ser Val Gly Gly Glu Lys Arg Asp Leu Glu Ile Glu Val Val
                        515                 520                 525

Leu Phe His Pro Asn Tyr Asn Ile Asn Gly Lys Lys Glu Ala Gly Ile
                530                 535                 540

Pro Glu Phe Tyr Asp Tyr Asp Val Ala Leu Ile Lys Leu Lys Asn Lys
        545                 550                 555                 560

Leu Lys Tyr Gly Gln Thr Ile Arg Pro Ile Cys Leu Pro Cys Thr Glu
                        565                 570                 575

Gly Thr Thr Arg Ala Leu Arg Leu Pro Pro Thr Thr Thr Cys Gln Gln
                        580                 585                 590

Gln Lys Glu Glu Leu Leu Pro Ala Gln Asp Ile Lys Ala Leu Phe Val
                        595                 600                 605

Ser Glu Glu Glu Lys Lys Leu Thr Arg Lys Glu Val Tyr Ile Lys Asn
                610                 615                 620

Gly Asp Lys Lys Gly Ser Cys Glu Arg Asp Ala Gln Tyr Ala Pro Gly
        625                 630                 635                 640

Tyr Asp Lys Val Lys Asp Ile Ser Glu Val Val Thr Pro Arg Phe Leu
                        645                 650                 655

Cys Thr Gly Gly Val Ser Pro Tyr Ala Asp Pro Asn Thr Cys Arg Gly
                        660                 665                 670

Asp Ser Gly Gly Pro Leu Ile Val His Lys Arg Ser Arg Phe Ile Gln
                        675                 680                 685

Val Gly Val Ile Ser Trp Gly Val Val Asp Val Cys Lys Asn Gln Lys
                690                 695                 700

Arg Gln Lys Gln Val Pro Ala His Ala Arg Asp Phe His Ile Asn Leu
        705                 710                 715                 720

Phe Gln Val Leu Pro Trp Leu Lys Glu Lys Leu Gln Asp Glu Asp Leu
                        725                 730                 735

Gly Phe Leu

<210> SEQ ID NO 2
<211> LENGTH: 234
<212> TYPE: PRT
<213> ORGANISM: Homo sapiens

<400> SEQUENCE: 2

Thr Pro Trp Ser Leu Ala Trp Pro Gln Gly Ser Cys Ser Leu Glu Gly
1               5                   10                  15

Val Glu Ile Lys Gly Gly Ser Phe Arg Leu Leu Gln Glu Gly Gln Ala
```

```
                20                  25                  30
Leu Glu Tyr Val Cys Pro Ser Gly Phe Tyr Pro Tyr Pro Val Gln Thr
            35                  40                  45
Arg Thr Cys Arg Ser Thr Gly Ser Trp Ser Thr Leu Lys Thr Gln Asp
        50                  55                  60
Gln Lys Thr Val Arg Lys Ala Glu Cys Arg Ala Ile His Cys Pro Arg
65                  70                  75                  80
Pro His Asp Phe Glu Asn Gly Glu Tyr Trp Pro Arg Ser Pro Tyr Tyr
                85                  90                  95
Asn Val Ser Asp Glu Ile Ser Phe His Cys Tyr Asp Gly Tyr Thr Leu
            100                 105                 110
Arg Gly Ser Ala Asn Arg Thr Cys Gln Val Asn Gly Arg Trp Ser Gly
        115                 120                 125
Gln Thr Ala Ile Cys Asp Asn Gly Ala Gly Tyr Cys Ser Asn Pro Gly
    130                 135                 140
Ile Pro Ile Gly Thr Arg Lys Val Gly Ser Gln Tyr Arg Leu Glu Asp
145                 150                 155                 160
Ser Val Thr Tyr His Cys Ser Arg Gly Leu Thr Leu Arg Gly Ser Gln
                165                 170                 175
Arg Arg Thr Cys Gln Glu Gly Gly Ser Trp Ser Gly Thr Glu Pro Ser
            180                 185                 190
Cys Gln Asp Ser Phe Met Tyr Asp Thr Pro Gln Glu Val Ala Glu Ala
        195                 200                 205
Phe Leu Ser Ser Leu Thr Glu Thr Ile Glu Gly Val Asp Ala Glu Asp
    210                 215                 220
Gly His Gly Pro Gly Glu Gln Gln Lys Arg
225                 230

<210> SEQ ID NO 3
<211> LENGTH: 504
<212> TYPE: PRT
<213> ORGANISM: Homo sapiens

<400> SEQUENCE: 3

Lys Ile Val Leu Asp Pro Ser Gly Ser Met Asn Ile Tyr Leu Val Leu
1               5                   10                  15
Asp Gly Ser Asp Ser Ile Gly Ala Ser Asn Phe Thr Gly Ala Lys Lys
            20                  25                  30
Cys Leu Val Asn Leu Ile Glu Lys Val Ala Ser Tyr Gly Val Lys Pro
        35                  40                  45
Arg Tyr Gly Leu Val Thr Tyr Ala Thr Tyr Pro Lys Ile Trp Val Lys
    50                  55                  60
Val Ser Glu Ala Asp Ser Ser Asn Ala Asp Trp Val Thr Lys Gln Leu
65                  70                  75                  80
Asn Glu Ile Asn Tyr Glu Asp His Lys Leu Lys Ser Gly Thr Asn Thr
                85                  90                  95
Lys Lys Ala Leu Gln Ala Val Tyr Ser Met Met Ser Trp Pro Asp Asp
            100                 105                 110
Val Pro Pro Glu Gly Trp Asn Arg Thr Arg His Val Ile Ile Leu Met
        115                 120                 125
Thr Asp Gly Leu His Asn Met Gly Gly Asp Pro Ile Thr Val Ile Asp
    130                 135                 140
Glu Ile Arg Asp Leu Tyr Ile Gly Lys Asp Arg Lys Asn Pro Arg Glu
145                 150                 155                 160
```

Asp Tyr Leu Asp Val Tyr Val Phe Gly Val Gly Pro Leu Val Asn Gln
            165                 170                 175

Val Asn Ile Asn Ala Leu Ala Ser Lys Lys Asp Asn Glu Gln His Val
        180                 185                 190

Phe Lys Val Lys Asp Met Glu Asn Leu Glu Asp Val Phe Tyr Gln Met
    195                 200                 205

Ile Asp Glu Ser Gln Ser Leu Ser Leu Cys Gly Met Val Trp Glu His
210                 215                 220

Arg Lys Gly Thr Asp Tyr His Lys Gln Pro Trp Gln Ala Lys Ile Ser
225                 230                 235                 240

Val Ile Arg Pro Ser Lys Gly His Glu Ser Cys Met Gly Ala Val Val
                245                 250                 255

Ser Glu Tyr Phe Val Leu Thr Ala Ala His Cys Phe Thr Val Asp Asp
            260                 265                 270

Lys Glu His Ser Ile Lys Val Ser Val Gly Gly Glu Lys Arg Asp Leu
        275                 280                 285

Glu Ile Glu Val Val Leu Phe His Pro Asn Tyr Asn Ile Asn Gly Lys
    290                 295                 300

Lys Glu Ala Gly Ile Pro Glu Phe Tyr Asp Tyr Asp Val Ala Leu Ile
305                 310                 315                 320

Lys Leu Lys Asn Lys Leu Lys Tyr Gly Gln Thr Ile Arg Pro Ile Cys
                325                 330                 335

Leu Pro Cys Thr Glu Gly Thr Thr Arg Ala Leu Arg Leu Pro Pro Thr
            340                 345                 350

Thr Thr Cys Gln Gln Gln Lys Glu Glu Leu Leu Pro Ala Gln Asp Ile
        355                 360                 365

Lys Ala Leu Phe Val Ser Glu Glu Lys Lys Leu Thr Arg Lys Glu
    370                 375                 380

Val Tyr Ile Lys Asn Gly Asp Lys Lys Gly Ser Cys Glu Arg Asp Ala
385                 390                 395                 400

Gln Tyr Ala Pro Gly Tyr Asp Lys Val Lys Asp Ile Ser Glu Val Val
                405                 410                 415

Thr Pro Arg Phe Leu Cys Thr Gly Gly Val Ser Pro Tyr Ala Asp Pro
            420                 425                 430

Asn Thr Cys Arg Gly Asp Ser Gly Gly Pro Leu Ile Val His Lys Arg
        435                 440                 445

Ser Arg Phe Ile Gln Val Gly Val Ile Ser Trp Gly Val Val Asp Val
    450                 455                 460

Cys Lys Asn Gln Lys Arg Gln Lys Gln Val Pro Ala His Ala Arg Asp
465                 470                 475                 480

Phe His Ile Asn Leu Phe Gln Val Leu Pro Trp Leu Lys Glu Lys Leu
                485                 490                 495

Gln Asp Glu Asp Leu Gly Phe Leu
            500

<210> SEQ ID NO 4
<211> LENGTH: 45
<212> TYPE: PRT
<213> ORGANISM: Homo sapiens

<400> SEQUENCE: 4

Lys Ile Val Leu Asp Pro Ser Gly Ser Met Asn Ile Tyr Leu Val Leu
1               5                   10                  15

Asp Gly Ser Asp Ser Ile Gly Ala Ser Asn Phe Thr Gly Ala Lys Lys
            20                  25                  30

Cys Leu Val Asn Leu Ile Glu Lys Val Ala Ser Tyr Gly
        35                  40                  45

<210> SEQ ID NO 5
<211> LENGTH: 200
<212> TYPE: PRT
<213> ORGANISM: Homo sapiens

<400> SEQUENCE: 5

Asn Ile Tyr Leu Val Leu Asp Gly Ser Asp Ser Ile Gly Ala Ser Asn
1               5                   10                  15

Phe Thr Gly Ala Lys Lys Cys Leu Val Asn Leu Ile Glu Lys Val Ala
            20                  25                  30

Ser Tyr Gly Val Lys Pro Arg Tyr Gly Leu Val Thr Tyr Ala Thr Tyr
        35                  40                  45

Pro Lys Ile Trp Val Lys Val Ser Glu Ala Asp Ser Ser Asn Ala Asp
    50                  55                  60

Trp Val Thr Lys Gln Leu Asn Glu Ile Asn Tyr Glu Asp His Lys Leu
65                  70                  75                  80

Lys Ser Gly Thr Asn Thr Lys Lys Ala Leu Gln Ala Val Tyr Ser Met
                85                  90                  95

Met Ser Trp Pro Asp Asp Val Pro Pro Glu Gly Trp Asn Arg Thr Arg
            100                 105                 110

His Val Ile Ile Leu Met Thr Asp Gly Leu His Asn Met Gly Gly Asp
        115                 120                 125

Pro Ile Thr Val Ile Asp Glu Ile Arg Asp Leu Leu Tyr Ile Gly Lys
    130                 135                 140

Asp Arg Lys Asn Pro Arg Glu Asp Tyr Leu Asp Val Tyr Val Phe Gly
145                 150                 155                 160

Val Gly Pro Leu Val Asn Gln Val Asn Ile Asn Ala Leu Ala Ser Lys
                165                 170                 175

Lys Asp Asn Glu Gln His Val Phe Lys Val Lys Asp Met Glu Asn Leu
            180                 185                 190

Glu Asp Val Phe Tyr Gln Met Ile
        195                 200

<210> SEQ ID NO 6
<211> LENGTH: 282
<212> TYPE: PRT
<213> ORGANISM: Homo sapiens

<400> SEQUENCE: 6

Leu Cys Gly Met Val Trp Glu His Arg Lys Gly Thr Asp Tyr His Lys
1               5                   10                  15

Gln Pro Trp Gln Ala Lys Ile Ser Val Ile Arg Pro Ser Lys Gly His
            20                  25                  30

Glu Ser Cys Met Gly Ala Val Val Ser Glu Tyr Phe Val Leu Thr Ala
        35                  40                  45

Ala His Cys Phe Thr Val Asp Asp Lys Glu His Ser Ile Lys Val Ser
    50                  55                  60

Val Gly Gly Glu Lys Arg Asp Leu Glu Ile Glu Val Val Leu Phe His
65                  70                  75                  80

Pro Asn Tyr Asn Ile Asn Gly Lys Lys Glu Ala Gly Ile Pro Glu Phe
                85                  90                  95

Tyr Asp Tyr Asp Val Ala Leu Ile Lys Leu Lys Asn Lys Leu Lys Tyr
            100                 105                 110

-continued

```
Gly Gln Thr Ile Arg Pro Ile Cys Leu Pro Cys Thr Glu Gly Thr Thr
        115                 120                 125
Arg Ala Leu Arg Leu Pro Pro Thr Thr Thr Cys Gln Gln Gln Lys Glu
        130                 135                 140
Glu Leu Leu Pro Ala Gln Asp Ile Lys Ala Leu Phe Val Ser Glu Glu
145                 150                 155                 160
Glu Lys Lys Leu Thr Arg Lys Glu Val Tyr Ile Lys Asn Gly Asp Lys
                165                 170                 175
Lys Gly Ser Cys Glu Arg Asp Ala Gln Tyr Ala Pro Gly Tyr Asp Lys
                180                 185                 190
Val Lys Asp Ile Ser Glu Val Val Thr Pro Arg Phe Leu Cys Thr Gly
        195                 200                 205
Gly Val Ser Pro Tyr Ala Asp Pro Asn Thr Cys Arg Gly Asp Ser Gly
        210                 215                 220
Gly Pro Leu Ile Val His Lys Arg Ser Arg Phe Ile Gln Val Gly Val
225                 230                 235                 240
Ile Ser Trp Gly Val Val Asp Val Cys Lys Asn Gln Lys Arg Gln Lys
                245                 250                 255
Gln Val Pro Ala His Ala Arg Asp Phe His Ile Asn Leu Phe Gln Val
                260                 265                 270
Leu Pro Trp Leu Lys Glu Lys Leu Gln Asp
        275                 280
```

ANTI-FACTOR BB ANTIBODIES

RELATED APPLICATION

This application is a Continuation-in-Part of U.S. Ser. No. 12/675,220, filed Feb. 25, 2010, which is a National Phase Filing of PCT/US2008/074489, filed Aug. 27, 2008, which claims priority from U.S. Provisional Application No. 60/968,146, filed Aug. 27, 2007, the subject matter of which are incorporated herein by reference in their entirety.

GOVERNMENT FUNDING

This invention was made with Government support under Grant No. R44HL080934; R44AR048476 awarded by the National Institutes of Health. The United States Government has certain rights to the invention.

FIELD OF THE INVENTION

The present invention relates to complement activation. Particularly, the present invention relates to the method for inhibiting complement activation via the alternative pathway. More particularly, the present invention relates to the use of antibodies for factor Bb for inhibiting the activity of C3bBb or PC3bBb complexes, inhibiting the proteolytic activity of Bb in C3/C5 convertases.

BACKGROUND OF THE INVENTION

The complement system is responsible for initiating and amplifying the inflammatory response to microbial infection and other acute insults. Inappropriate activation of complement has been implicated in pathological situations. For instance, the complement system has been implicated in contributing to the pathogenesis of several acute and chronic conditions, including atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, and macular degeneration.

Complement can be activated through three distinct enzymatic cascades, referred to as the "classical", "Lectin/MBL", and "alternative" pathways (CP, MBL, and AP respectively). These pathways are shown schematically in FIG. 1. The AP is responsible for 80-95% of total complement activity. Both classical and alternative pathways have the ability to produce C3a and C5a. However, the level of these anaphylatoxins varies depending upon which pathway is active. Lectin pathway is a variation of the classical pathway. Alternative pathway is activated in a number of disease indications. There are three specific proteins Factors B, D, and P that play a major role in the initiation and propagation of the AP. The terminal complex is known as MAC which is responsible for lysis. Both C3a and C5a are potent anaphylatoxins that are responsible for activating platelets, neutrophils, and monocytes. As a result, inflammatory molecules such as elastase, TNF, IL-1, VEGF, and peroxides are released.

FIG. 2 illustrates a schematic of AP activation. As a result of C3 tick over, C3b is generated. In the schematic, assumption has been made that tick-over of C3 and cleavage of C3 generates the same activated C3b with the released C3a. Activated C3b binds properdin oligomers present in blood to generated (P)n (C3b)n complex. Factor B having higher affinity to properdin bound C3b makes the complex PC3bB, which is then cleaved by factor D to generate PC3bBb. This active convertase cleaves additional C3 to make C3b and release C3a. The same C3 convertase with additional C3b molecules forms C5 convertase. The C5 convertase or C3 convertase cleave C5 to make C5b and C5a. The C5b molecule inserts into the lipid bilayer and forms the nucleus for MAC deposition.

Factor B is composed of two discrete domains Ba (molecular weight, 33 kDa) and Bb (molecular weight, 60 kDa). The Ba domain consists of three short consensus repeats known as SCR1, SCR2, and SCR3 (FIG. 3). It has been shown, using mutation analysis and with the use of specific Ba monoclonal antibodies that the factor B functional domain is located in the SCR3 region. Such region was used to produce antibodies that demonstrated clinical benefit in several animal models of diseases. The Bb domain of factor B contains the Von Willowbrand (VWF) domain in addition to the serine protease domain. It is clear from various studies that it is the Ba domain that is important for factor B function, and that inhibition of factor B binding to C3b was required for inhibition of complement activity.

Properdin, a small but important molecule binds C3b to form P-C3b complex and such binding is high affinity. Factor B binds both free C3b and P-C3 to form C3bB and PC3bB complexes. These complexes are cleaved by factor D to form, C3bBb and PC3bBb, both of which possess C3-convertase activity. The resulting convertase can cleave C3, into C3b and C3a. The newly produced C3b fragment, which covalently attaches to the target and then interacts with factors B and D to form the additional alternative pathway C3 convertase molecules.

It is known that the alternative pathway C3-convertase is stabilized by C3b-bound properdin. Since the substrate for the alternative pathway C3-convertase is C3, C3 is therefore both a component and a product of the reaction. As the C3-convertase generates increasing amounts of C3b, an amplification loop is established. Furthermore, the classical pathway can also generate C3b which can bind factor B and thereby engage the alternative pathway even though the trigger is CP mediated. This allows more C3b to deposit on a target leading to enhanced amplification of AP activation. All three, the classical, the lectin, and the alternative pathways converge at C3, which is cleaved by the C3 convertase to form C3b and C3a. C3a is a potent anaphylatoxin and has been implicated in the pathogenesis of a variety of clinical indications. C3a activates neutrophils, monocytes, platelets, mastcells, and T lymphocytes. C3a has been shown to be important for the induction of paw edema in an adjuvant-induced arthritis model.

Addition of newly formed C3b to the existing C3 convertase forms C5 convertase, which cleaves C5 to produce C5b and C5a. C5a similar to C3a is also a potent anaphylatoxin that causes alterations in smooth muscle, in vascular tone, and in vascular permeability. It is also a powerful chemotaxin and an activator of neutrophils, monocytes, platelets, endothelial cells, and T lymphocytes. C5a-mediated cellular activation can significantly amplify inflammatory responses by inducing the release of additional inflammatory mediators, including cytokines, hydrolytic enzymes, arachadonic acid metabolites and reactive oxygen species.

The cleavage of C5 produces C5b and C5a. Anaphylatoxin C5a is released and C5b inserts itself into the lipid bilayer and acts as a nucleus for C6, C7, C8, and C9 deposition to form the C5b-9 complex at the surface of the target cell. C5b-9 is also known as the membrane attack complex (MAC). There is now strong evidence that MAC may play an important role in inflammation in addition to its role as a lytic pore-forming complex. In addition to the proven role of C3a, C5a in platelet activation, C5b-9 is also known to mediate activation of platelets. Thus, there is significant evidence suggesting C3a, C5a, and MAC involvement in activation of platelets. Regardless of the method of platelet activation, activated platelets express CD62P also called P-selectin. P-selectin also mediates platelet-monocyte conjugation, and such binding triggers the release of tissue factor from monocytes. One result of such conjugate formation is the removal of platelets from the circulation, a phenomenon that can contribute to the development of thrombocytopenia.

While complement activation provides a valuable first-line defense against potential pathogens, the activities of complement that promote a protective inflammatory response can also represent a potential threat to the host. For example, C3a and C5a anaphylatoxins recruit and activate neutrophils, monocytes and platelets to the pathological site. These activated cells are indiscriminate in their release of destructive enzymes and may cause organ damage. Currently, there are no approved drugs exist that can inhibit the damages caused by the inappropriate activation of the complement pathway. Based upon the available clinical data, it appears that in most acute injury settings, complement activation is mediated predominantly via the alternative pathway. Therefore, developing suitable methods that inhibit only this pathway without completely obviating the immune defense capabilities would be highly desirable. This would leave the classical pathway intact to handle immune complex processing and to aid in host defense against infection.

Factor B plays a key role in the amplification loop of the alternative pathway since it provides the catalytic subunit, Bb, for the C3-convertase (PC3bBb). Since factor B is an essential component of the alternative pathway, it presents an attractive target for specifically inhibiting this pathway. Factor B by itself is a zymogen with no known catalytic activity, but after binding to PC3b complex, factor B is cleaved by factor D to release Ba. It has been shown that factor B binds C3b through regions found within each of the Ba and Bb subunits. Inhibitors of factor Bb binders should results in selective inhibition of factor B function thereby preventing formation of C3a, C5a and C5b-9, which are responsible for many deleterious effects mentioned previously. Based on the results described in this patent application, it should be possible to develop anti-Bb specific inhibitors or inhibition methods that (a) will prevent factor B function by blocking PC3bBb activity and/or (b) suppress factor B cleavage that prevent Bb generation. These inhibitors appear to be inactivators of the C3 convertase enzymatic activity without disrupting the factor B interaction with C3b.

We have evaluated the inhibitory activity of the anti-factor Bb antibodies for their potential role in blocking the AP activation. These antibodies prevent factor B function both in vitro and in whole blood. Other anti-factor Ba monoclonal antibodies have also been developed and tested in animal models of disease. These antibodies prevent factor B binding to C3b and hence block the activation of the complement cascade.

SUMMARY OF THE INVENTION

The present invention relates to a process of inhibiting the adverse effects of alternative complement pathway activation products in a subject. The process includes administering to the subject an amount of anti-factor Bb antibody effective to selectively inhibit formation of an alternative complement pathway activation products C3a, C5a, and C5b-9, and activation of neutrophils, monocytes, and platelets. The anti-factor Bb antibody can selectively bind Bb motif of Factor B.

In an aspect of the invention, the anti-factor Bb antibody can a motif in a fusion protein comprising at least one of a factor D cleavage site of factor B, a VWF domain of factor B, or serine protease domain of factor B. The anti-factor Bb antibody does not bind the Ba motif of the factor B. The anti-factor Bb antibody also does not prevent Factor B or Bb binding to C3b/PC3b.

The anti-factor Bb antibody can be a full antibody or an antigen-binding fragment of an anti-factor Bb antibody. The antibody can be a chimeric, deimmunized, humanized, fully human, or truncated antibody. The fragmented antibody can include F(ab), F(ab'), F(ab)2, F(ab')2, Fv, single chain fragment, or truncated F(ab)2 or F(ab')2 fragment.

The amount of the anti-factor Bb antibody administered to the subject is effective to selectively inhibit the activity of alternative complement C3 convertase C3bBb or PC3bBb, does not inhibit the classical complement pathway, reduces the levels of catalytically active PC3bBb/C3bBb complex and increases the levels of catalytically inactive PC3bBb/C3bBb complexes, prevents the formation of additional C3b and PC3b, increases the clearance of the complex C3bBb-antifactor Bb agent via the CR1 receptors on erythrocytes, inhibit formation of anaphylatoxins C3a and C5a, and membrane attack complex C5b-9 or sC5b-9, and prevent activation of neutrophils, monocytes, and platelets.

The adverse effects of complement activation treated by the anti-factor B antibody can include a disease or condition selected from the group consisting of atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, macular degeneration, spontaneous abortion and combinations thereof.

The present invention also relates to a method of inhibiting alternative complement pathway activation in a mammal. The method includes administering to a mammal an amount of an antibody and/or fragment thereof that specifically binds to an epitope of Bb segment of the factor B effective to inhibit alternative complement pathway in the mammal.

The antibody can be monoclonal. The antibody can also be chimeric, recombinant, humanized, de-immunized, fully human, or truncated antibody. The antibody fragment can include F(ab), F(ab'), F(ab)2, F(ab')2, Fv, single chain fragment, truncated F(ab)2, IgG, or truncated IgG.

The ratio of antibody binding to factor B can be about 0.5:1 to about 2:1. Administration of the antibody to the mammal can result in at least one of the following: factor B binding to C3b is not inhibited, the formation of C3bB is reduced, C3bBb formation is reduced, C3a and C5a production is reduced, C5b-9 complex formation is reduced, activation of neutrophils is reduced, activation of monocytes is reduced, activation of platelets is reduced, formation of leukocyte-platelet conjugates is reduced, or Ba production is reduced. The antibody can also inhibit alternative pathway dependent rabbit erythrocyte lysis in human serum/plasma and be administered in vivo or ex vivo.

The present invention further relates to a method of inhibiting alternative complement pathway activation in a mammalian host by administering to the host a therapeutically effective amount of an anti-factor Bb monoclonal antibody that specifically binds to an epitope within the serine protease domain of Bb. The antibody can be monoclonal. The antibody can also be chimeric, recombinant, humanized, de-immunized, fully human, or truncated antibody. The antibody fragment can include F(ab), F(ab'), F(ab)2, F(ab')2, Fv, single chain fragment, truncated F(ab)2, IgG, or truncated IgG.

The ratio of antibody binding to factor B can be about 0.5:1 to about 2:1. Administration of the antibody to the mammal can result in at least one of the following: factor B binding to C3b is not inhibited, the formation of C3bB is reduced, C3bBb formation is reduced, C3a and C5a production is reduced, C5b-9 complex formation is reduced, activation of neutrophils is reduced, activation of monocytes is reduced, activation of platelets is reduced, formation of leukocyte-platelet conjugates is reduced, or Ba production is reduced. The antibody can also inhibit alternative pathway dependent rabbit erythrocyte lysis in human serum/plasma and be administered in vivo or ex vivo.

The present invention still further relates to a method of inhibiting alternative complement pathway activation in a mammal by administering to the mammal a therapeutically effective amount of the anti-factor Bb monoclonal antibody that specifically binds to the catalytic triad Asp-His-Ser in the serine protease domain of factor B and its Bb fragment. The antibody can be monoclonal. The antibody can also be chimeric, recombinant, humanized, de-immunized, fully human, or truncated antibody. The antibody fragment can include F(ab), F(ab'), F(ab)2, F(ab')2, Fv, single chain fragment, truncated F(ab)2, IgG, or truncated IgG.

The ratio of antibody binding to factor B can be about 0.5:1 to about 2:1. Administration of the antibody to the mammal can result in at least one of the following: the formation of C3bB is reduced by way of reduced formation of C3b, C3 convertase formation is reduced, C3a and C5a production is reduced, C5b-9/C5b-9 complex formation is reduced, activation of neutrophils is reduced, activation of monocytes is reduced, activation of platelets is reduced, or formation of leukocyte-platelet conjugates is reduced. The antibody can also inhibit alternative pathway dependent rabbit erythrocyte lysis in human serum/plasma and be administered in vivo or ex vivo.

The present invention also relates to a method of inhibiting alternative complement pathway activation in a mammalian subject by administering to the subject a therapeutically effective amount of the anti-factor Bb monoclonal antibody that specifically binds to an epitope within the serine protease domain of Bb. The antibody can be monoclonal. The antibody can also be chimeric, recombinant, humanized, de-immunized, fully human, or truncated antibody. The antibody fragment can include F(ab), F(ab'), F(ab)2, F(ab')2, Fv, single chain fragment, truncated F(ab)2, IgG, or truncated IgG.

The ratio of antibody binding to factor B can be about 0.5:1 to about 2:1. Administration of the antibody to the mammal can result in at least one of the following: the formation of C3bB is reduced by way of reduced formation of C3b, C3 convertase formation is reduced, C3a and C5a production is reduced, C5b-9/C5b-9 complex formation is reduced, activation of neutrophils is reduced, activation of monocytes is reduced, activation of platelets is reduced, or formation of leukocyte-platelet conjugates is reduced. The antibody can also inhibit alternative pathway dependent rabbit erythrocyte lysis in human serum/plasma and be administered in vivo or ex vivo.

Yet another aspect of the present invention relates to a method of inhibiting alternative complement pathway activation in a mammal by administering to the mammal an amount of an antibody or fragment thereof that specifically binds to Bb and inhibits C3b oligomer formation by way of preventing formation of additional C3b molecules which otherwise would associate with existing C3b to form oligomers. The C3b oligomers can contain two or more C3b monomers.

In an aspect of the invention, the antibody specifically binds to an epitope on the Bb sequence. The epitope includes at least a portion of the amino acid sequence of serine protease domain or VWA domain. The anti-factor Bb binding to Bb prevents production of additional C3b monomers.

The antibody can be monoclonal. The antibody can also be chimeric, recombinant, humanized, de-immunized, fully human, or truncated antibody. The antibody fragment can include F(ab), F(ab'), F(ab)2, F(ab')2, Fv, single chain fragment, truncated F(ab)2, IgG, or truncated IgG.

The ratio of antibody binding to factor B can be about 0.5:1 to about 2:1. Administration of the antibody to the mammal can result in at least one of the following: the formation of C3bB is reduced by way of reduced formation of C3b, C3 convertase formation is reduced, C3a and C5a production is reduced, C5b-9/C5b-9 complex formation is reduced, activation of neutrophils is reduced, activation of monocytes is reduced, activation of platelets is reduced, or formation of leukocyte-platelet conjugates is reduced. The antibody can also inhibit alternative pathway dependent rabbit erythrocyte lysis in human serum/plasma and be administered in vivo or ex vivo.

Another aspect of the present invention relates to a method of treating alternative pathway activation mediated by disease-related or pathological conditions. The method includes administering to the mammal a therapeutically effective amount of an antibody or fragment thereof that specifically binds to an epitope of Bb that blocks the alternative pathway activation without affecting the classical pathway activation.

The antibody can be monoclonal. The antibody can also be chimeric, recombinant, humanized, de-immunized, fully human, or truncated antibody. The antibody fragment can include F(ab), F(ab'), F(ab)2, F(ab')2, Fv, single chain fragment, truncated F(ab)2, IgG, or truncated IgG.

The ratio of antibody binding to factor B can be about 0.5:1 to about 2:1. Administration of the antibody to the mammal can result in at least one of the following: the formation of C3bB is reduced by way of reduced formation of C3b, C3 convertase formation is reduced, C3a and C5a production is reduced, C5b-9/C5b-9 complex formation is reduced, activation of neutrophils is reduced, activation of monocytes is reduced, activation of platelets is reduced, or formation of leukocyte-platelet conjugates is reduced. The antibody can also inhibit alternative pathway dependent rabbit erythrocyte lysis in human serum/plasma and be administered in vivo or ex vivo.

The disease or condition treated can be selected from the group consisting of atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, macular degeneration, and combinations thereof.

The present invention further relates to an isolated antibody or antigen binding portion thereof that includes the heavy chain variable regions and the light chain variable regions of an antibody produced by the hybridoma cell line deposited under ATCC Accession Number PTA-8543.

The antibody can be monoclonal. The antibody can also be chimeric, recombinant, humanized, de-immunized, fully human, or truncated antibody. The antibody fragment can include F(ab), F(ab'), F(ab)2, F(ab')2, Fv, single chain fragment, truncated F(ab)2, IgG, or truncated IgG.

The ratio of antibody binding to factor B can be about 0.5:1 to about 2:1. Administration of the antibody to the mammal can result in at least one of the following: the formation of C3bB is reduced by way of reduced formation of C3b, C3 convertase formation is reduced, C3a and C5a production is reduced, C5b-9/C5b-9 complex formation is reduced, activation of neutrophils is reduced, activation of monocytes is reduced, activation of platelets is reduced, or formation of leukocyte-platelet conjugates is reduced. The antibody can also inhibit alternative pathway dependent rabbit erythrocyte lysis in human serum/plasma and be administered in vivo or ex vivo.

BRIEF DESCRIPTION OF THE DRAWINGS

FIG. 37 illustrates NM001 competes with biotinylated NM001.

FIG. 38 illustrates NM001 does not compete with NM1209.

DETAILED DESCRIPTION OF THE INVENTION

Figure 1:
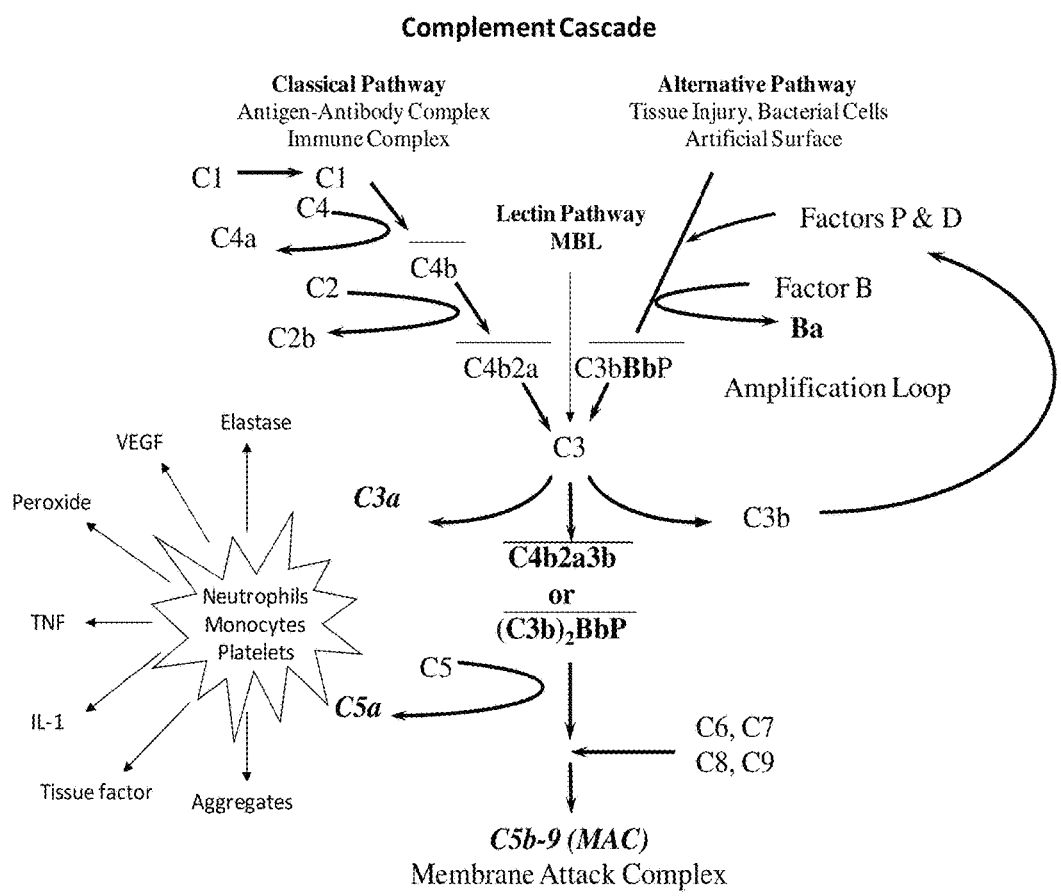
FIG. 1 is a schematic illustration of the complement pathway.
Figure 2:
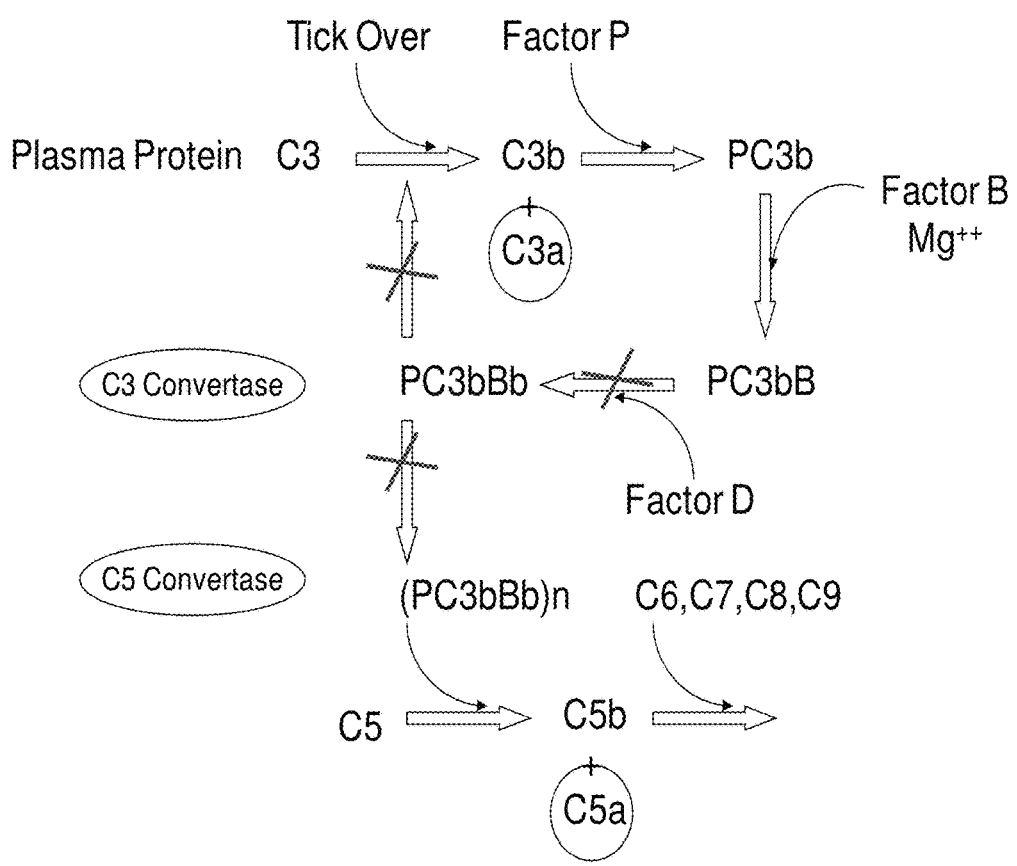
FIG. 2 is a schematic illustration of alternative complement activation.

The term "polypeptide" is used herein as a generic term to refer to native protein, fragments, or analogs of a polypeptide sequence. Hence, native protein, fragments, and analogs are species of the polypeptide genus.

The term "polypeptide fragment" as used herein refers to a polypeptide that has an amino-terminal and/or carboxyl-terminal deletion, but where the remaining amino acid sequence is identical to the corresponding positions in the naturally occurring sequence deduced, for example, from a full-length properdin sequence. Fragments typically are at least 5, 6, 8 or 10 amino acids long, preferably at least 14 amino acids long, more preferably at least 20 amino acids long, usually at least 50 amino acids long, and even more preferably at least 70 amino acids long.

"Antibody" or "antibody peptide(s)" refer to an intact antibody, or a binding fragment thereof that competes with the intact antibody for specific binding. Binding fragments are produced by recombinant DNA techniques, or by enzymatic or chemical cleavage of intact antibodies. Binding fragments include Fab, Fab', F(ab')$_2$, Fv, single-chain antibodies, truncated antibodies and F(ab')$_2$ truncated antibodies. An antibody other than a "bispecific" or "bifunctional" antibody is understood to have each of its binding sites identical.

The term "monoclonal" refers to an antibody that binds to a sequence of amino acid and has a single specific epitope on its target antigen. For example, NM001 is a monoclonal antibody that is specific Bb domain of factor B. Because the antibody is monoclonal, it would recognize a domain/motif that contains the sequence contained in Bb (SEQ ID NO: 3).

The term "polyclonal" refers to an antibody that recognizes multiple epitope sites on a single antigen. For example, a polyclonal antibody against Bb indicates that the antibody will bind several sites of the Bb.

The term "epitope" includes any protein determinant capable of specific binding to an immunoglobulin. Epitope determinants usually consist of chemically active surface groupings of molecules such as amino acids or sugar side chains and usually have specific three-dimensional structural characteristics, as well as specific charge characteristics.

The terms "oligomer" and "polymer" are used interchangeable. The terms "oligomer" and "polymer" refer to the association of more than one monomer of a specific protein, peptide, or peptide fragments. The terms "oligomer" and "polymer" in this invention specifically relates to the ability of properdin protein monomers to form protein complexes with it or with other proteins.

The term "agent" is used herein to denote a chemical compound, a mixture of chemical compounds, a biological macromolecule, or an extract made from biological materials.

The terms "patient," "mammalian host," and the like are used interchangeably herein, and refer to mammals, including human and veterinary subjects.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The term "a disease or disorder associated with the alternative complement pathway," as used herein, refers to a disease or disorder caused, directly or indirectly, by activation of the alternative complement pathway, a disease or disorder that is mediated, directly or indirectly, by one or more components of the alternative complement pathway, or a product generated by the alternative complement pathway. The term also refers to a disease or disorder that is exacerbated by one or more components of the alternative complement pathway, or a product generated by the alternative complement pathway.

The term "knockout" refers to the technique in which a specific gene(s) are removed from a target animal. This technique is usually applied to rodents in which the gene of interest is removed via homologous recombination of an empty vector with the native animal chromosome. The technique works by swapping the animal's chromosome containing the gene with the empty vector containing a marker or random DNA sequences. This method results in an animal that is deficient of the gene of interest. The present invention would utilize this technique to generate antibodies against an antigen that is removed from the animal's genome to enhance generation of antibodies.

It is to be understood that this invention is not limited to particular embodiments described, as such may, of course, vary. It is also to be understood that the terminology used herein is for describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are encompassed within the invention, subject to any specifically excluded limit in the stated range. Where the stated range includes one or both of the limits, ranges excluding either or both of those included limits are also included in the invention.

The present invention relates to a method of a method of inhibiting alternative complement pathway activation in a mammal, inhibiting the adverse effects of alternative complement pathway activation products, and/or treating alternative pathway activation mediated by disease-related or pathological conditions. The method includes administering to a mammal an anti-factor Bb agent that inhibits the function of C3b/PC3b bound Bb, inhibits the function of PC3bBb by blocking its proteolytic activity, inhibits the factor D cleavage of factor B, inhibits the formation of C3a, C3b, C5a, C5b-9, and sC5b-9, inhibits the formation of C3bBb and PC3bBb, inhibiting the formation of Ba, inhibits the formation of Bb, inhibits the properdin-induced oligomerization of C3b, and inhibitis the activation of neutrophils, monocytes, and platelets in clinical conditions where the disease pathology is complement-mediated.

Factor B is a 90 kDa protein that can have an amino acid sequence of SEQ ID NO: 1. Factor B consists of three domains (FIG. 3): a three-module complement control protein (CCP1, CCP2, and CCP3), a von Willebrand factor A domain (e.g., SEQ ID NO: 5), and a C-terminal serine protease (SP) domain (e.g., SEQ ID NO: 6) that adopts a default inactive (zymogen) conformation. The interaction between factor B and surface-bound C3b triggers a conformational change in factor B that ultimately creates the "C3 convertase" (PC3bBb) of the alternative complement pathway. The activation of the alternative pathway of complement (AP) hinges on a Magnesium ion-enhanced interaction between factor B and C3b. Upon binding, factor B is rendered susceptible to proteolytic cleavage by factor D, forming fragments Ba (30 kDa) (e.g., SEQ ID NO: 2) and Bb (60 kDa) (e.g., SEQ ID NO: 3). Bb, in association with C3b, comprises the AP C3 convertase. This complex has serine protease activity and functions to cleave native C3 into C3a and C3b.

Factor B is activated through an assembly process: it binds surface-bound C3b after which it is cleaved by factor D into fragments Ba (residues 26-234; SEQ ID NO: 2) and Bb (residues 235-739 SEQ ID NO: 3). Fragment Ba dissociates from the complex, leaving behind the alternative pathway C3 convertase complex C3b-Bb, which cleaves C3 into C3a and C3b. This protease complex is intrinsically instable. Once dissociated from the complex, Bb cannot reassociate with C3b. The proenzyme factor B consists of three N-terminal complement control protein (CCP: 1, 2, and 3) domains, connected by a 45-residue linker (SEQ ID NO: 4) to a VWA domain and a C-terminal serine protease (SP) domain, which carries the catalytic center triad (ASP-HIS-SER). The VWA and SP domains form fragment Bb, and CCP1 through CCP3 and the linker form fragment Ba. Binding of factor B to C3b depends on elements in fragment Ba and the Mg2+-dependent metal ion-dependent adhesion site (MIDAS) motif in the VWA domain of fragment Bb.

In both intact Factor B and Bb, serine protease domain is exposed and the catalytic site is freely accessible to small substrates. The two structures differ markedly in the orientation of the VWA-SP region. In active state, the cleaved Bb exposes the catalysis site even further and is fully functional to now allow cleavage of further C3 molecules into C3a and C3b. Inhibition of Bb activity by anti-factor Bb agent will prevent the formation of C3a and C3b.

Figure 3:
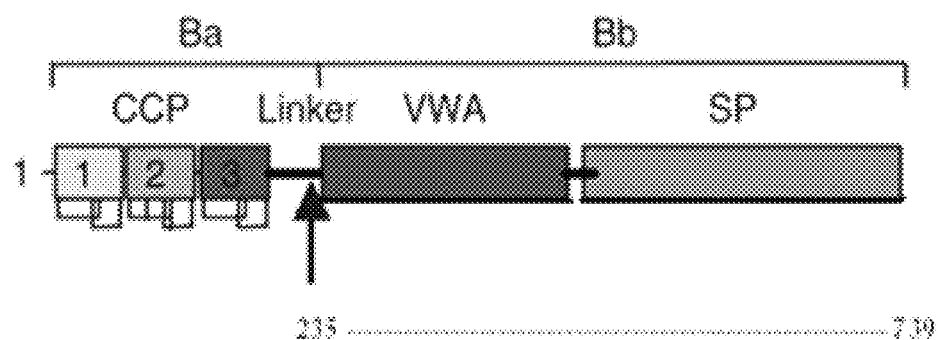
FIG. 3 illustrates the schematic of factor B. The Bb segment of Factor B contains the VWA and serine protease regions.
Figure 4A:
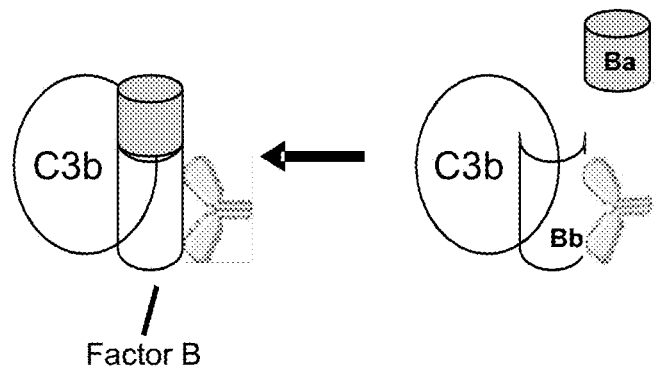
FIG. 4A is a schematic illustration of the mechanism of interaction of the monoclonal antibody with Factor B and its fragment Bb and FIG. 4B is a schematic illustration of the mechanism of interaction of a prior art monoclonal antibody with Factor B and its fragment Ba.
Figure 4B:
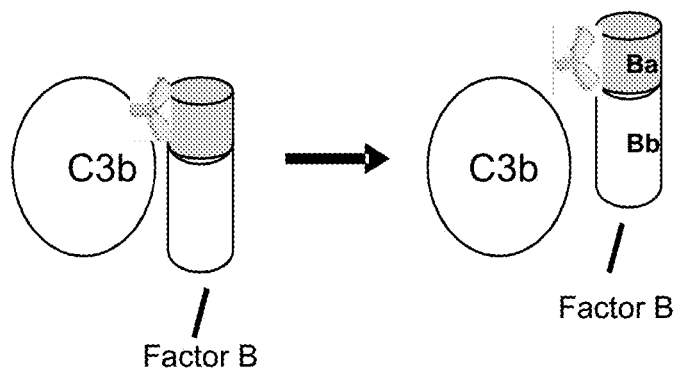

In accordance with an aspect of the invention, the anti-factor Bb agent can include an anti-factor Bb antibody that is directed to or specifically binds to Bb domain of factor B. The anti-factor B antibody of this invention binds the Bb fragments, does not bind Ba fragment, does not inhibit the factor B binding to C3b, inhibits C3b production, inhibits C3a, C5a, C5b-9 formation and inhibits lysis of rabbit erythrocytes. FIG. 3 is schematic illustration of mechamisms of action the anti-factor B antibody. FIG. 3 shows that the anti-factor Bb antibody can inhibit the alternative pathway by binding the Bb domain in native Factor B and blocking the Factor D cleavage, binding the catalytic triad in the serine protease domain and preventing its action on C3 cleavage and hence halting C3b production, or binding the catalytic triad and locking the conformation such that cleavage of Factor B cannot occur. In contrast, as illustrated in FIG. 4B, prior art anti-Ba antibody does not bind the Bb segment and is involved only in Factor B binding to C3b. The anti-factor Bb antibody of present invention, however, does not inhibit the binding of Factor B to C3b.

The anti-factor B antibody of the present invention can also inhibit oligomerization of C3b. The molecular weight of native C3 is in the order of 190 kDa, upon cleavage by the convertase, C3 is converted into a C3a (10 kDa) and C3b (180 kDa). This C3b molecule has high affinity for properdin oligomers, as a result forms a complex containing 3 C3b molecules attached to a properdin trimer. The molecular weight of each properdin monomer is nearly 50,000. Considering the spatial arrangement of PC3b complex, it would seem feasible to construct a model in which all three C3b molecules are close together almost in an oligomer form.

Anti-factor Bb monoclonal antibodies of the present invention prevent formation of additional molecules of C3b and therefore result in a complex where C3b oligomer will not form. If C3b formation is completely prevented properdin will float alone without any C3b attached. Properdin does not bind C3 or the isoforms of C3b.

Figure 5:
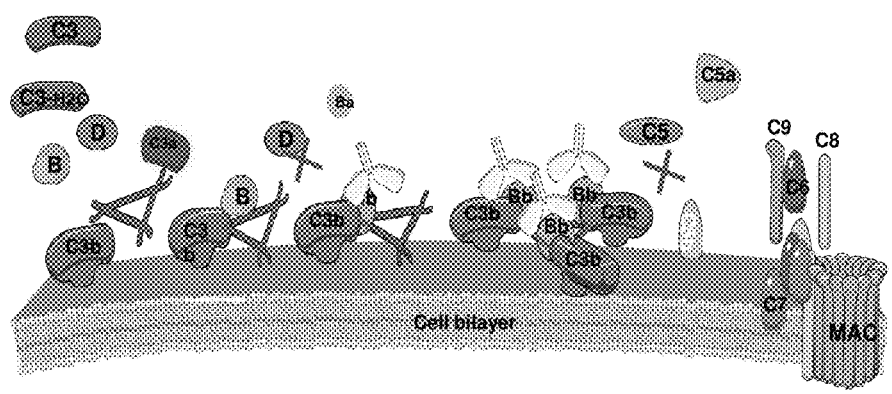
FIG. 5 illustrates the inactivation of PC3bBb by the monoclonal antibody of the present invention.

In another aspect, the anti-factor B antibody can bind to the serine protease domain and particularly the catalytic triad of serine protease of the Bb region. The mechanism of action of the anti-factor B antibody once bound to the serine protease domain is shown in FIG. 5. The serine protease domain forms the third and the last domain of intact factor B. The serine protease domain carries the catalytic site which is solely responsible for C3 cleavage. While the catalytic site is exposed in both intact factor B and the Bb fragment, it becomes active only after the Ba is cleaved off by factor D.

The anti-factor B antibody of the present invention can bind the catalytic triad and prevent its activity by either locking the inactive conformation in place or by binding to the region where factor D cleaves the factor B. The development of a monoclonal antibody that specifically recognizes the catalytic triad is a surprising discovery because limited number of highly target specific protease inhibitory monoclonal antibodies have been discovered. The anti-factor Bb antibody can be highly target specific in that it only cross reacts to human factor B and shows no cross reactivity to rat, rabbit, guinea pig, dog, baboon, rhesus, and cynomologous monkey. These findings are of high importance and suggests that anti-factor Bb antibody is a highly target specific antibody. For such antibodies, animal data is not required for moving into the clinical trial for human safety and efficacy.

In another aspect of the invention, the anti-factor Bb antibody can be specific to inhibiting the alternative pathway and not inhibit the classical pathway, which is generally required for host defense against infection. The anti-factor Bb antibody can also inhibit C3a, C5a, and C5b-9 and cellular activation. Both C3a and C5a are potent anaphylatoxins that are generated during the AP activation. Regardless of the trigger/initiator of the AP, if C3a, C5a and C5b-9 are formed in excessive amounts above control levels, damage to cellular systems occurs. Neutrophils bear the C5a receptor and therefore respond to compounds that prevent C5a production or antibodies that neutralize the C5a or the receptor antagonists that prevent receptor attack by C5a. Similarly, platelets have the C3a receptors and therefore agents that prevent/neutralize C3a activity would prevent platelet activation. Monocytes have C3a receptors and upon activation release "TNF" and "IL-1" which have been implicated in inflammatory diseases such as arthritis. Secretory components such as neutrophil elastase, TNF, and IL-1 have been defined as the markers of inflammation. In addition activated neutrophils, monocytes and platelets orchestrate the inflammatory responses by forming leukocyte-platelet conjugates. In a number of clinical diseases, all these cell types are known.

Anti-factor Bb antibodies of the present invention can include murine human anti-factor Bb monoclonal antibodies, and compositions comprising the antibodies. The anti-factor Bb antibody can be produced by an antibody-producing hybridoma. Chimeric, de-immunized, single chain, truncated, fully human and humanized versions of the anti-factor Bb antibody can be generated by those skilled in the art. Human/humanized/chimerized anti-factor Bb antibody avoids problems associated with rodent antibodies, i.e., adverse reactions in humans, such as hypersensitivity reactions, including urticaria, dyspnea, hypotension, anaphylaxis, and the like.

An example of an anti-factor Bb antibody in accordance with the present invention that specifically binds to the Bb region was isolated as described in the Examples. The Examples of the present application disclose an anti-factor Bb antibody identified as NM001 that is produced by the hybridoma cell line 1 D3 deposited under ATCC Accession Number PTA-8543, on Jul. 18, 2007 at 10801 University Boulevard, Manassa, Va. 20110-2209, under the terms of the Budapest Treaty. NM001 and an F(ab)2 fragment of NM001 (Bikaciomab) surprisingly bind in the factor Bb region of the molecule and show no reactivity to the peptide Ba. As shown in the Examples, NM001 and the F(ab)2 fragment do not cross react with rat, mouse, rabbit, dog, pig, baboon sera. However, NM001 and the F(ab)2 fragment exclusively cross react with Cynomologus and Human thereby making it a highly specific to humans. NM001 and the F(ab)2 fragment were found to inhibit C3b production, inhibit C3a production, inhibit C5a production, inhibit C5b-9 production, inhibit sC5b-9 production, inhibit TNF production, inhibit Elastase production, inhibit neutrophil activation, inhibit monocyte activation, and inhibit platelet activation.

Another aspect of the invention relates to antibodies that bind to the same epitope on Bb as the NM001. Such antibodies can be identified based on their ability to cross-compete with NM001 in standard Bb binding assays. The ability of a test antibody to inhibit the binding of NM001 to Bb demonstrates that the test antibody can compete with NM001 for binding to Bb and thus binds to the same epitope on Bb as NM001.

For example, an anti-Bb antibody or antigen binding portion thereof that competitively inhibits binding of an anti-Bb antibody or antigen binding portion thereof can occur when biotinylated NM001 binds Bb and this binding is inhibited by another antibody. Although the definition can be used by those skilled in the art for developing inhibitors that bind the site occupied by NM001. Thus, demonstration in an in vitro assay can easily translate the inhibitors effect in vivo.

In an aspect of the invention, the antibody that binds to the same epitope on Bb as NM001 is a human monoclonal antibody. Such human monoclonal antibodies can be prepared and isolated as described in the Examples.

In yet another aspect, an antibody of the invention can comprise heavy and light chain variable regions comprising amino acid sequences that are homologous to the amino acid sequences of the preferred antibodies described herein, and wherein the antibodies retain the desired functional properties of the anti-factor Bb antibodies of the invention. For example, the invention provides an isolated monoclonal antibody, or antigen binding portion thereof, comprising a heavy chain variable region and a light chain variable region, wherein: (a) the heavy chain variable region comprises an amino acid sequence that is at least 80% homologous to the amino acid sequence of heavy chain of NM001 (b) the light chain variable region comprises an amino acid sequence that is at least 80% homologous to the amino acid sequence of NM001; and (c) the antibody specifically binds to the Bb region of factor B.

In various aspects, the antibody can be, for example, a human antibody, a humanized antibody or a chimeric antibody. In other aspects, the VH and/or VL amino acid sequences may be 85%, 90%, 95%, 96%, 97%, 98% or 99% homologous to the sequences set forth above. An antibody having VH and VL regions having high (i.e., 80% or greater)

homology to the VH and VL regions of the sequences set forth above, can be obtained by mutagenesis (e.g., site-directed or PCR-mediated mutagenesis) of nucleic acid molecules the heavy and light chain of NM001, followed by testing of the encoded altered antibody for retained function (i.e., the functions set forth in (c) and (d) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

In certain aspects, an antibody of the invention can include a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein (e.g., NM001). In a more specific example, the heavy chain variable region CDR2 sequence comprises the amino acid sequence of heavy chain of NM001, or conservative modifications thereof; and the light chain variable region CDR2 sequence comprises the amino acid sequence light chain of NM001, or conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (j) above) using the functional assays described herein.

An antibody of the invention further can be prepared using an antibody having one or more of the VH and/or VL sequences disclosed herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Thus, such antibodies contain the VH and VL CDR sequences of NM001 may contain different framework sequences from these antibodies.

Another type of variable region modification is to mutate amino acid residues within the VH and/or VK CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) are introduced. The mutations may be amino acid substitutions, additions or deletions, but are preferably substitutions. Moreover, typically no more than one, two, three, four or five residues within a CDR region are altered.

Anti-factor Bb monoclonal antibodies can be prepared by standard methods well known in the art. For example, rodents (e.g. mice, rats, hamsters, and guinea pigs) can be immunized either with factor B, or factor Bb purified from human plasma or urine or with recombinant factor B or its fragments expressed by either eukaryotic or prokaryotic systems. Antibodies specific to factor Bb can be identified by selecting those that do not bind the Ba. The antibody product of the present invention does not bind the Ba region of the protein. Other animals can also be used for immunization, e.g., non-human primates, transgenic mice expressing human immunoglobulins, and severe combined immunodeficient mice transplanted with human B-lymphocytes. Hybridoma can be generated by conventional procedures well known in the art by fusing B lymphocytes from the immunized animals with myeloma cells (e.g., Sp2/0 and NS0). In addition, anti-factor Bb antibodies can be generated by screening of recombinant single-chain $F_v$ or $F_{ab}$ libraries from human B lymphocytes in phage-display systems. The specificity of the MoAbs to human factor Bb can be tested by enzyme linked immunosorbent assay (ELISA).

In the antibody molecule, there are four chains. The amino-terminal portion of each chain includes a variable region of 100 to 110 amino acids responsible for antigen recognition. The carboxyl-terminal portion of each chain defines a constant region primarily responsible for effector function. Thus, an intact antibody has two binding sites. Except in bifunctional or bispecific antibodies, the two binding sites are the same. A bispecific or bifunctional antibody is an artificial hybrid antibody having two different heavy/light chain pairs and two different binding sites. Bispecific antibodies can be produced by a variety of methods including fusion of hybridomas or linking of Fab' fragments. Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human antibodies can be prepared that avoid certain of the problems associated with antibodies that possess murine or rat variable and/or constant regions. An important practical application of such a strategy is the "humanization" of the mouse humoral immune system. Introduction of human immunoglobulin (Ig) loci into mice in which the endogenous IgG genes have been inactivated offers the opportunity to study the mechanisms underlying programmed expression and assembly of antibodies as well as their role in B-cell development. Furthermore, such a strategy could provide an ideal source for production of fully human monoclonal antibodies (MoAbs)—an important milestone towards fulfilling the promise of antibody therapy in human disease. Fully human antibodies are expected to minimize the immunogenic and allergic responses intrinsic to mouse or mouse-derivatized MoAbs and thus to increase the efficacy and safety of the administered antibodies. The use of fully human antibodies can be expected to provide a substantial advantage in the treatment of chronic and recurring human diseases, such as inflammation, autoimmunity, and cancer, which require repeated antibody administrations.

One approach towards this goal is to engineer mouse strains deficient in mouse antibody production with large fragments of the human IgG loci in anticipation that such mice would produce a large repertoire of human antibodies in the absence of mouse antibodies. Large human IgG fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human MoAbs with the desired specificity could be readily produced and selected.

Human anti-mouse antibody (HAMA) responses: While chimeric antibodies have a human constant region and a murine variable region, it is expected that certain human anti-chimeric antibody (HACA) responses will be observed, particularly in chronic or multi-dose utilizations of the antibody. Thus, it would be desirable to provide fully human antibodies against Bb in order to vitiate concerns and/or effects of HAMA or HACA response.

Humanization and Display Technologies

As was discussed above in connection with human antibody generation, there are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art.

Antibody fragments, such as Fv, F(ab').sub.2 and Fab may be prepared by cleavage of the intact protein, e.g. by protease or chemical cleavage. Alternatively, a truncated gene is designed. For example, a chimeric gene encoding a portion of the F(ab').sub.2 fragment would include DNA sequences encoding the CH1 domain and hinge region of the H chain, followed by a translational stop codon to yield the truncated molecule.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art.

Additional Criteria for Antibody Therapeutics

As discussed herein, the function of a subject anti-Bb antibody appears important to at least a portion of its mode of operation. By function, we mean, by way of example, the activity of the anti-Bb antibody in inhibiting the alternative complement pathway, e.g., a subject anti-Bb antibody exhibits one or more of the following properties: (a) inhibiting the function of C3b/PC3b bound Bb; (b) inhibiting the function of PC3bBb by blocking its proteolytic activity, (c) inhibiting the factor D cleavage of factor B, (d) inhibiting the formation of C3a, C3b, C5a, C5b-9, and sC5b-9, (e) inhibiting the formation of C3bBb and PC3bBb, (f) inhibiting the formation of Ba, (g) inhibiting the formation of Bb, (h) inhibiting the properdin-induced oligomerization of C3b, and (i) inhibiting the activation of neutrophils, monocytes, and platelets Design and Generation of Other Therapeutics Other therapeutic modalities beyond antibody moieties can be facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules. In connection with the generation of advanced antibody therapeutics, where complement fixation is a desirable attribute, it may be possible to sidestep the dependence on complement for cell killing using bispecifics, immunotoxins, or radiolabels, for example.

Bispecific antibodies can be generated that comprise (i) two antibodies one with a specificity to Bb and another to a second molecule that are conjugated together, (ii) a single antibody that has one chain specific to Bb and a second chain specific to a second molecule, or (iii) a single chain antibody that has specificity to Bb and the other molecule. Such bispecific antibodies can be generated using techniques that are well known for example, in connection with (i) and (ii) and in connection with (iii).

In connection with the generation of therapeutic peptides, through the utilization of structural information related to Bb and antibodies thereto, such as the antibodies of the invention (as discussed below in connection with small molecules) or screening of peptide libraries, therapeutic peptides can be generated that are directed against Bb.

Assuming that the Bb molecule (or a form, such as a splice variant or alternate form) is functionally active in a disease process, it will also be possible to design gene and antisense therapeutics thereto through conventional techniques. Such modalities can be utilized for modulating the function of Bb.

Therapeutic Administration and Formulations

It will be appreciated that the therapeutic entities in accordance with the invention will be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as Lipofectin), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, if the active ingredient in the formulation is not inactivated by the formulation and the formulation is physiologically compatible and tolerable with the route of administration.

Preparation of Antibodies

Antibodies in accordance with the invention are prepared in mouse using standard methods well know in the art. The monoclonal antibody of the present invention will be converted into a humanized version for therapeutic use. The antibody can be made by contract or in house into humanized, fully human, chimeric, recombinant for therapeutic use. The hybridoma cell lines discussed herein are readily generated by those of ordinary skill in the art, given the guidance provided herein. Each of the antibodies produced by the subject cell lines are those that do not generate an adverse response. Adverse response is defined as unwanted responses which means in this invention an antibody type that can inhibit alternative pathway complement activation.

Antibodies in accordance with the present invention can be expressed in cell lines other than hybridoma cell lines. Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive Bb binding properties.

The results of the present invention indicate that antibodies can be made more efficacious than currently available antibodies against Bb and therefore will be efficacious in treating disorders associated with and/or mediated by the alternative complement pathway.

Therapeutic Uses

Anti-factor Bb antibodies can be used to treat diseases where AP participates in disease pathology. The anti-factor Bb antibodies can also be used in the treatment of many immunological disorders, either direct such as anaphylactic shock, rheumatoid arthritis, and the like, or secondary ones resulting from primary clinical conditions such as cardiopulmonary bypass inflammation, burn injury, and the like. The diseases treated by factor Bb inhibitors include, but are not limited to myocardial infarction, ischemia/reperfusion injury; vascular stenosis or post-angioplasty restenosis; stroke; acute respiratory distress syndrome (ARDS); sepsis; burn injury; cardiopulmonary bypass inflammation; extracorporeal circulation such as hemodialysis, plasmapheresis, plateletpheresis, leukopheresis, extracorporeal membrane oxygenation (ECMO), or heparin-induced extracorporeal LDL precipitation (HELP); allergic response to the use of radiographic contrast media; transplant rejection; other inflammatory conditions and autoimmune/immune complex diseases that are closely associated with complement activation such as multiple sclerosis, myasthemia gravis, pancreatitis, rheumatoid arthritis, Alzheimer's disease, asthma, spontaneous abortion, pain, neuronal and nerve cord injury, thermal injury, anaphylactic shock, bowel inflammation, urticaria, angioedema, vasculitis, and Sjogren's syndrome, lupus erythromatosus, membranous nephritis, and dermatomysitis.

Treatment Methods

The methods generally involve administering to a mammalian subject in need thereof an effective amount of a subject antibody for including methods of reducing the level of a polypeptide generated following activation of the alternative complement pathway; methods of reducing the level of membrane attack complex (MAC); methods of reducing the level of an anaphylatoxin; methods of reducing the level of C3c; and methods of treating a disease or disorder mediated by the alternative complement pathway.

An "effective amount" of a subject antibody is an amount that is effective to reduce the production and/or level of a polypeptide generated following activation of the alternative complement pathway by at least about 20%, at least about 30%, at least about 40%, at least about 50%, at least about 60%, at least about 70%, at least about 80%, at least about 90%, or more.

A subject antibody is administered to an individual in a formulation with a pharmaceutically acceptable excipient(s). A wide variety of pharmaceutically acceptable excipients are known in the art and need not be discussed in detail herein.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In the subject methods, a subject antibody may be administered to the host using any convenient means capable of resulting in the desired therapeutic effect. Thus, the antibody can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of a subject antibody can be achieved in various ways, including oral, buccal, rectal, parenteral, intraperitoneal, intradermal, subcutaneous, intramuscular, transdermal, intranasal, pulmonary, intratracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject antibody calculated in an amount sufficient to produce the desired effect in association with a pharmaceutically acceptable diluent, carrier or vehicle.

A subject antibody is administered to an individual at a frequency and for a period of time so as to achieve the desired therapeutic effect. For example, a subject antibody is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid), or substantially continuously, or continuously, over a period of time ranging from about one day to about one week, from about two weeks to about four weeks, from about one month to about two months, from about two months to about four months, from about four months to about six months, or longer.

Combination Therapy

The anti-factor Bb antibody will in some embodiments be administered in an effective amount in combination therapy with a second therapeutic agent. Suitable second therapeutic agents include, but are not limited to, anti-inflammatory agents; agents used for the treatment of cardiovascular disorders; steroidal anti-inflammatory agents; and the like.

Suitable anti-inflammatory agents include, but are not limited to, non-steroidal anti-inflammatory drugs (NSAIDs) acetaminophen, salicylate, acetyl-salicylic acid (aspirin, diflunisal), ibuprofen, Motrin, Naprosyn, Nalfon, and Trilisate, indomethacin, glucametacine, acemetacin, sulindac, naproxen, piroxicam, diclofenac, benoxaprofen, ketoprofen, oxaprozin, etodolac, ketorolac tromethamine, ketorolac, nabumetone, and the like, and mixtures of two or more of the foregoing. Other suitable anti-inflammatory agents include methotrexate.

Suitable steroidal anti-inflammatory agents include, but are not limited to, hydrocortisone, prednisone, prednisolone, methylprednisolone, dexamethasone, betamethasone, and triamcinolone.

Examples agents for cardiovascular indications include GP IIb-IIIa inhibitors such as INTEGRILIN (eptifibatide); aprotinin; REOPRO (abciximab); and the like.

Suitable second therapeutic agents include beta adrenergics which include bronchodilators including albuterol, isoproterenol sulfate, metaproterenol sulfate, terbutaline sulfate, pirbuterol acetate and salmeterol formotorol; steroids including beclomethasone dipropionate, flunisolide, fluticasone, budesonide and triamcinolone acetonide.

Anti-inflammatory drugs used in connection with the treatment of respiratory diseases include steroids such as beclomethasone dipropionate, triamcinolone acetonide, flunisolide and fluticasone. Other examples of anti-inflammatory drugs include cromoglycates such as cromolyn sodium. Other respiratory drugs, which would qualify as bronchodilators, include anticholenergics including ipratropium bromide. Antihistamines include, but are not limited to, diphenhydramine, carbinoxamine, clemastine, dimenhydrinate, pryilamine, tripelennamine, chlorpheniramine, brompheniramine, hydroxyzine, cyclizine, meclizine, chlorcyclizine, promethazine, doxylamine, loratadine, and terfenadine. Particular anti-histamines include rhinolast (Astelin), claratyne (Claritin), claratyne D (Claritin D), telfast (Allegra), zyrtec, and beconase.

In some embodiments, the anti-factor Bb antibody is administered concurrently with a second therapeutic agent. As used herein, the term "concurrently" indicates that the subject antibody and the second therapeutic agent are administered separately and are administered within about 5 seconds to about 15 seconds, within about 15 seconds to about 30 seconds, within about 30 seconds to about 60 seconds, within about 1 minute to about 5 minutes, within about 5 minutes to about 15 minutes, within about 15 minutes to about 30 minutes, within about 30 minutes to about 60 minutes, within about 1 hour to about 2 hours, within about 2 hours to about 6 hours, within about 6 hours to about 12 hours, within about 12 hours to about 24 hours, or within about 24 hours to about 48 hours of one another.

In some embodiments, the anti-factor Bb antibody is administered during the entire course of treatment with the second therapeutic agent. In other embodiments, a subject antibody is administered for a period of time that is overlapping with that of the treatment with the second therapeutic agent, e.g., the antibody treatment can begin before the treatment with the second therapeutic agent begins and end before the treatment with the second therapeutic agent ends; the antibody treatment can begin after the treatment with the second therapeutic agent begins and end after the antibody treatment ends; the antibody treatment can begin after the treatment with the second therapeutic agent begins and end before the treatment with the second therapeutic agent ends; or antibody treatment can begin before the treatment with the second therapeutic agent begins and end after the treatment with the second therapeutic agent ends.

Subjects for Treatment

Subjects that can be treated with the anti-factor Bb antibody and combination therapies of the present invention include individuals suffering from one or more of the following disorders: atherosclerosis, ischemia-reperfusion following acute myocardial infarction, Henoch-Schonlein purpura nephritis, immune complex vasculitis, rheumatoid arthritis, arteritis, aneurysm, stroke, cardiomyopathy, hemorrhagic shock, crush injury, multiple organ failure, hypovolemic shock and intestinal ischemia, transplant rejection, cardiac Surgery, PTCA, spontaneous abortion, neuronal injury, spinal cord injury, myasthenia gravis, Huntington's disease, amyotrophic lateral sclerosis, multiple sclerosis, Guillain Barre syndrome, Parkinson's disease, Alzheimer's disease, acute respiratory distress syndrome, asthma, chronic obstructive pulmonary disease, transfusion-related acute lung injury, acute lung injury, Goodpasture's disease, myocardial infarction, post-cardiopulmonary bypass inflammation, cardiopulmonary bypass, septic shock, transplant rejection, xeno transplantation, burn injury, systemic lupus erythematosus, membranous nephritis, Berger's disease, psoriasis, pemphigoid, dermatomyositis, anti-phospholipid syndrome, inflammatory bowel disease, hemodialysis, leukopheresis, plasmapheresis, heparin-induced extracorporeal membrane oxygenation LDL precipitation, extracorporeal membrane oxygenation, and macular degeneration.

In an a particular aspect of the invention, subjects that can be treated with a subject method include individuals suffering from one or more of the following disorders: post-cardiopulmonary bypass inflammation, myocardial infarction, stroke, acute respiratory distress syndrome (ARDS), septic shock, transplant rejection, burn injury, multiple sclerosis, myasthenia gravis, cardiovascular disorders, and rheumatoid arthritis. Subjects suitable for treatment with a subject method also include individuals suffering from any inflammatory disorder, including, but not limited to, systemic lupus erythematosus, membranous nephritis, pemphigoid, dermatomyositis, and anti-phospholipid syndrome. Subjects suitable for treatment also include subjects undergoing renal dialysis.

INCORPORATION BY REFERENCE

All references cited herein, including patents, patent applications, papers, textbooks, and the like, and the references cited therein, to the extent that they are not already, are hereby incorporated herein by reference in their entirety. In addition, the following references are also incorporated by reference herein in their entirety, including the references cited in such references:

EQUIVALENTS

The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

EXAMPLES

The examples which follow are presented to describe preferred embodiments and utilities of the invention and are not meant to limit the invention unless otherwise stated in the claims appended hereto. The description is intended as a non-limiting illustration, since many variations will become apparent to those skilled in the art in view thereof. It is intended that all such variation within the scope and spirit of the appended claims be embraced thereby. Changes can be made in the composition, operation, and arrangement of the method of the present invention described herein without departing from the concept and scope of the invention as defined in the claims.

Unless stated otherwise all reagents were ultrapure. All complement reagents are from Complementech, Tylar Tex. or from Quidel Corporation, San Diego, Calif. GVB for classical pathway, Phosphate bueffferd saline was purchased from Sigma-Aldrich, St Louise Mo., GVB for alternative complement pathway was purchased from Complemmentech, Tylar, Tex., All flow cytometry antibodies were from BD Biosciences, San Jose, Calif., TMB substrate was from Kirkegaard & Perry Limited, Gaithersberg, Md., rRBC and sheep erythrocytes (antibody sensitized) were from Complementech, Tylar, Tex., All secondary antibodies were from American Qualex, San Clemente, Calif., BSA and other reagents were all from Sigma-Aldrich, St Louise, Mo. Normal Human serum was freshly isolated using BD Biosciences Clotting tubes.

ELISA plate readers (SpectraMax 190 and 250) were from Molecular Devices, and Flow Cytometer was FACSCalibur. Varity 3D program was used for data analyses, Curve fittings were done using MicroCal Origin program. Hemolysis kinetic assay was run using SectraMax, Molecular Devices, ELISA plates were from Corning Costar, Lowell, Mass.

It would be evident to the one skilled in the art that in vitro studies of complement are representative of and predictive of the in vivo state of the complement system. By way of example, the use of in vitro ELISA (Enzyme Linked Immunosorbent Assay) procedures to detect factor Bb associated with lipopolysaccharide (LPS) is a "simple, rapid and reliable method for the assessment of complement function particularly the detection of complement deficiency states". Thus, the in vitro technique can be used in vivo with the same likelihood of success in detecting alternative complement pathway activation in disease states. Furthermore, the standard rabbit erythrocyte hemolysis assay, which assay is used to measure alternative complement pathway activity, is accepted in the art as being the "most convenient assay for the activity of the human alternative pathway".

Example 1

Assembly of C3 Convertase

Interactions of Factor B, C3b and Properdin

It is known that Factor B binds C3b. It is also known that properdin binds C3b and that C3 convertase (PC3bBb) is stabilized in the presence of properdin. It has been debated whether properdin binds first or it binds after the C3bBb convertase is already formed. It is known that if AP activation does not proceed, C3b begins to degrade by the action of factors H and I into iC3b, C3c, and C3dg. The conversion of C3b into smaller fragments is indicative of degradation route of C3b. It is assumed that in a given system at a given time, there would be some degraded C3b components could exist. We evaluated whether B would bind C3b and PC3b with different affinities. We also evaluated iC3b, C3c, and C3dg for factor B binding in the presence and absence of properdin.

Factor B Binding to C3b and PC3b Using ELISA Based Binding Assays

Figure 6:
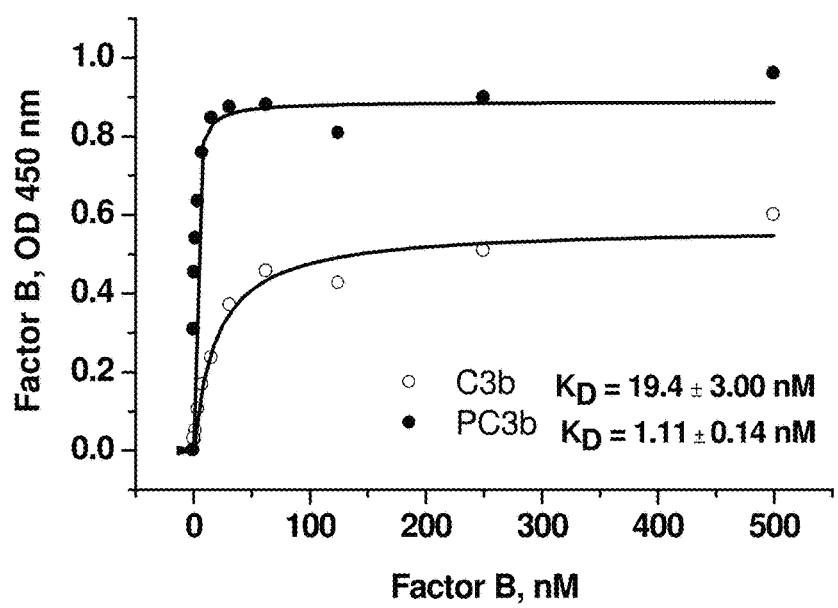
FIG. 6 shows the binding of Factor B to C3b and PC3b. Properdin Bound C3b with High Affinity: Factor B has a higher affinity towards properdin bound C3b. Various concentrations of factor B were added to plates coated with C3b and Properdin −C3b. Properdin bound C3b enhances the binding of factor B to C3b by ~20 fold. In this assay, the Kd of binding to C3b is ~19.4 nM and the binding to properdin bound C3b is 1.11 nM.

In the first experiment (FIG. 6), wells were coated with C3b (1 µg/50 µl per well) overnight. The plates were blocked with 1% BSA in PBS. After aspirating the protein solution, the wells were washed and incubated with factor B in the presence or absence of properdin (5 nM final). Following a 2 h incubation at room temperature, the wells were washed and incubated with the anti-properdin #2 antibbody from Quidel corporation at 1:2000 dilution in blocking solution. Following a 1 h incubation, the plate was rinsed with PBS and incubated with HRPO conjugated goat anti-mouse monoclonal antibody at 1:2000 dilution in blocking solution. Again, after a 1 h incubation, the wells were rinsed with PBS and the color was developed with TMB substrate using standard procedure. As shown in FIG. 6, the affinity of B binding to C3b is higher in cases when properdin is attached to C3b. We wanted to determine if properdin would bind the factor B. As shown in FIG. 6, Factor B binds with high affinity to properdin bound C3b.

Factor B Binding to Properdin

Figure 7:
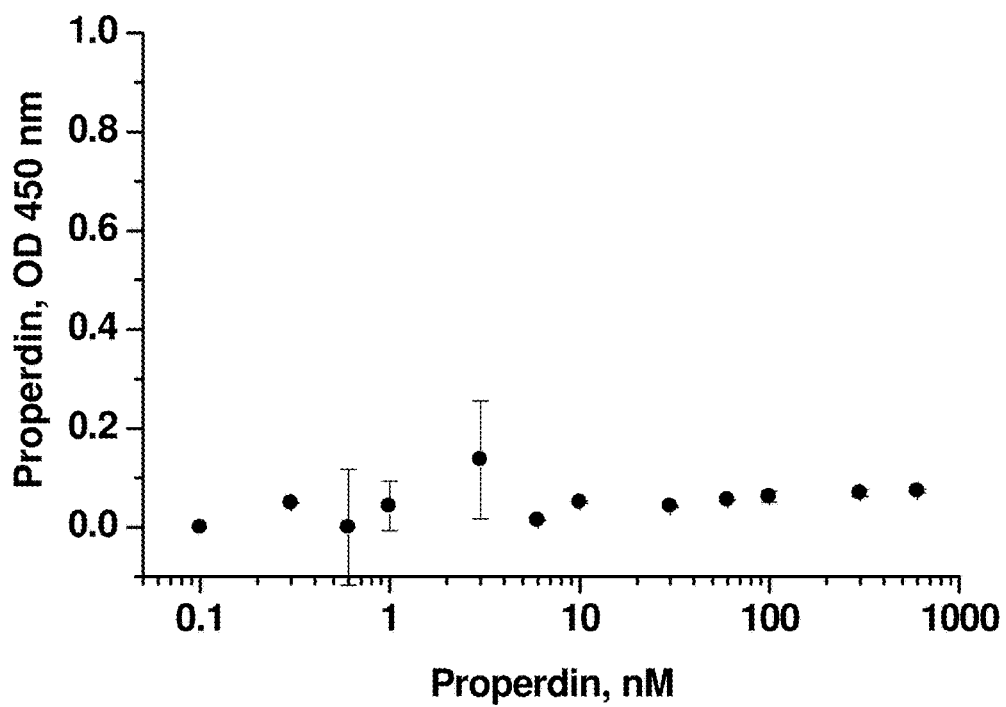
FIG. 7 shows that the high affinity binding of Factor B to PC3b over C3b is not due to direct supportive binding of properdin to factor B. Rather, properdin does not bind Factor B at any of the concentrations tested.

ELISA wells were coated with Factor B (2 µg/50 µl/well). The plate was incubated in cold overnight. The plate was blocked with 1% BSA in PBS for 2 hours at room temperature. ELISA wells were incubated with properdin in various concentrations. The plate was incubated for 2 hours, following which properdin was detected as above. As shown, properdin does not bind factor B (FIG. 7)

Factor B Binding to Isoforms of C3b which are iC3b, C3c, C3dg

Figure 8:
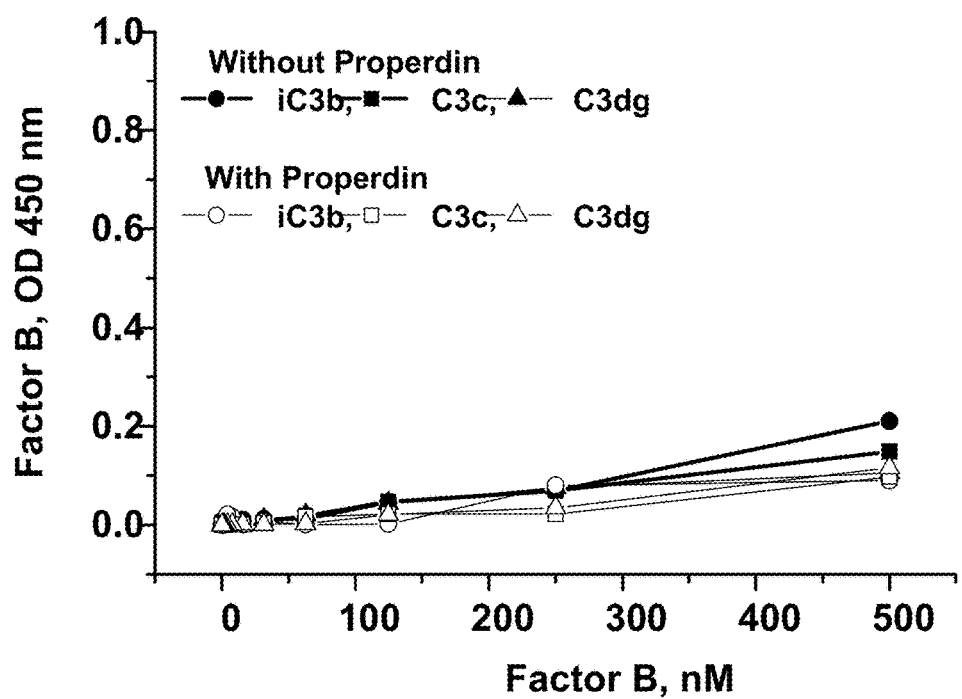
FIG. 8 shows that factor B does not bind C3b isoforms in the presence or absence of properdin: In this figure, increasing concentrations of Factor B were incubated with substrate-bound iC3b, C3c and C3dg. As shown, Factor B showed the lack of high affinity binding to C3b isoforms.

Polystyrene microtiter plates were coated with human iC3b, C3c, or C3dg (1.0 µg/50 µl per well) in phosphate buffered saline (PBS) overnight at 4° C. Following blocking and washing using standard methods, aliquots of factor B at varying concentration in AP buffer were added and plates were allowed to incubate for 2 hours. Factor B binding to various C3 isoforms was measured by adding detection antibody (Quidel, San Diego, Calif., anti-human factor B antibody) at 1:2000 dilution in blocking solution. The plate was allowed to incubate for 1 hour at room temperature. After washing the plates with PBS, a peroxidase-conjugated goat anti-mouse antibody (1:2000 dilution in blocking solution) was added and allowed to incubate for 1 hour. The plate was again rinsed thoroughly with PBS, and 100 µl of 3,3',5,5'-tetramethyl benzidine (TMB) substrate was added. After incubation for 30 minutes at 25 C., the reaction of TMB was quenched by the addition of 100 µl of phosphoric acid, and the plate was read at 450 nm in a microplate reader. In a separate experiment to evaluate the effect of the presence of properdin, an aliquot of properdin 5 nM was incubated for 1 hour in blocking solution on C3b isoforms coated plates. Following washing with PBS five times, various concentrations of factor B were added as above and the rest of the assay was performed as described above. FIG. 8 demonstrates that factor B does not bind any isoform of C3b except the protein C3b.

Example 2

Screening and Selection of Anti-Factor Bb Monoclonal Antibodies

Figure 9:
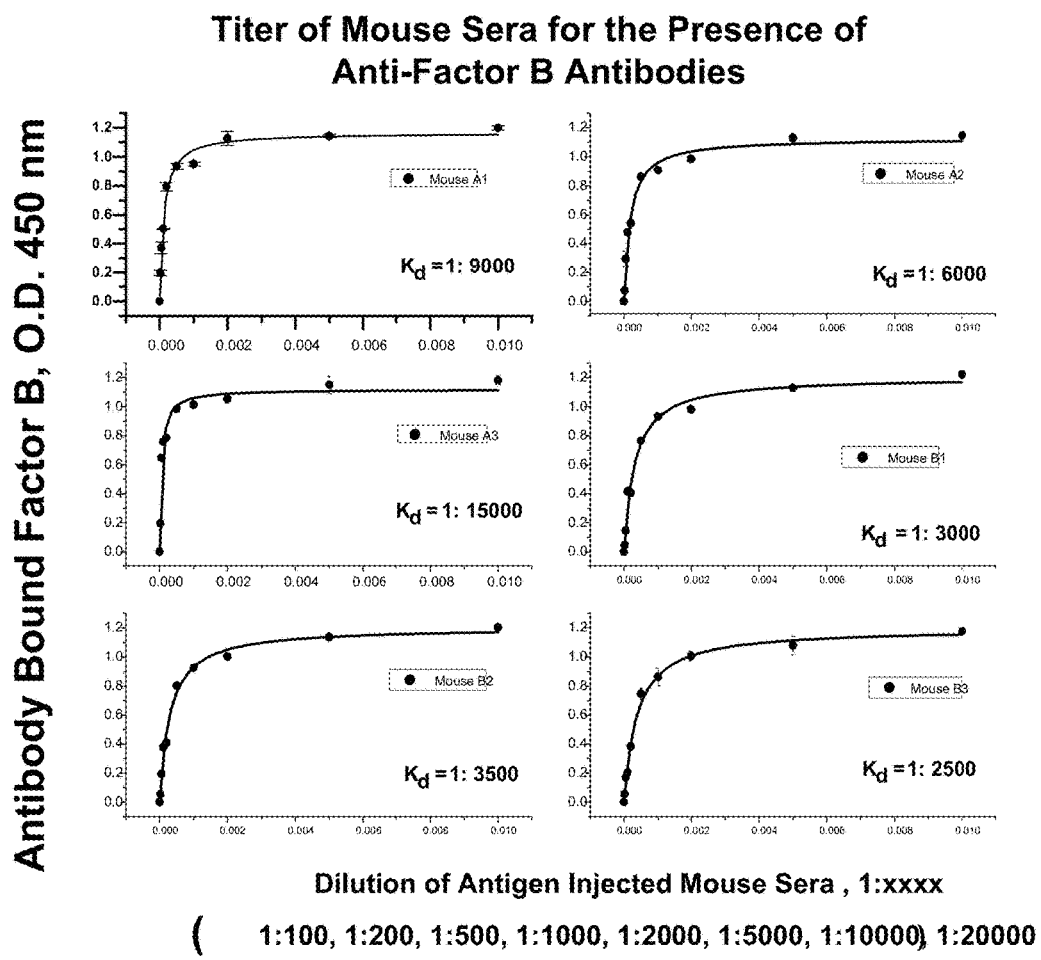
FIG. 9 illustrates making of monoclonal antibodies in mice. Monoclonal antibodies to Bb were made using standard procedure. All six mice, received the same treatment and sera from each of the six mice was evaluated for factor B binding. This figure represents the binding affinity of the mouse serum to human factor B. The titer of the sera was evaluated by incubating the factor B coated plates with mouse serum diluted up to 1:20,000 dilution. The half maximum was evaluated by hyperbola curve fitting.

Six mice were injected with Factor B antigen. Mice sera were removed and evaluated for factor B binding as shown in FIG. 9. All sera containing the mouse serum were diluted and incubated with factor B coated plates. The binding of anti-factor B monoclonal was determined with Peroxidase-conjugated goat anti-mouse IgG. The data was plotted using MicroCal Origin program. In a typical assay, polystyrene microtiter plates were coated with human factor B (2 µg/50 µl per well, (Complement Technologies, San Diego, Calif.) in phosphate buffered saline (PBS) overnight. After aspirating the factor B solution, wells were blocked with PBS containing 1% bovine serum albumin (BSA) (Sigma Chemical Company, St. Louis, Mo., Cat. No. A7888) for 2 hours at room temperature. Wells without factor B coating served as background controls. Aliquots of diluted hybridoma supernatants in blocking solutions at various dilutions were added to factor B-coated wells and plates were allowed to sit for 1 hour to allow the monoclonal antibody to bind the substrate-bound factor B. The plate was rinsed with PBS and factor B-bound monoclonal was detected by the addition of mouse monoclonal anti-human factor B antibody (detection antibody) (Quidel, San Diego, Calif., anti-human factor B monoclonal) at 1:2000 dilution in blocking solution, which was allowed to incubate for 1 hour at room temperature. After washing the plates with PBS, a peroxidase-conjugated goat anti-mouse antibody (1:1000 dilution in blocking solution) (Sigma Chemical Company) was added and allowed to incubate for 1 hour. The plate was again rinsed thoroughly with PBS, and 100 µl of 3,3',5,5'-tetramethyl benzidine (TMB) substrate (Kirkegaard & Perry Laboratories, Gaithersburg, Md., Cat. No. A50-65-00) was added. After incubation for 10 minutes at 25° C., the reaction of TMB was quenched by the addition of 100 µl of phosphoric acid, and the plate was read at 450 nm in a microplate reader (e.g., SPECTRA MAX 250, Molecular Devices, Sunnyvale, Calif.). Sera from all six mice bound factor B with low dilutions of serum. As shown in FIG. 9, all mice demonstrated comparable titer.

Figure 10:
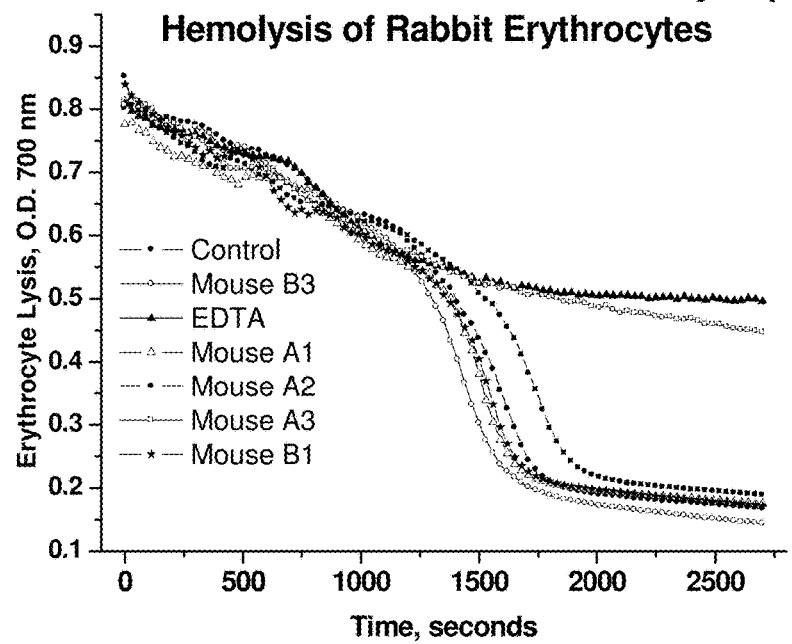
FIG. 10 illustrates inhibition of AP Dependent Hemolysis by Mice Sera: As shown, serum from only one mouse out of six used, inhibited AP dependent hemolysis. This figure demonstrates that the serum of only one mouse (A3) was capable of inhibiting hemolysis of rabbit erythrocytes. In this assay normal human serum in AP buffer is incubated with rabbit erythrocytes at 37 degree in a temperature controlled ELISA plate reader. As a result, AP activation, C5b-9 is formed on the erythrocyte surface causing lysis of the erythrocytes. The monoclonal antibody which interferes with the AP activation should prevent such lysis. Serum from mouse #A3 prevented lysis of erythrocytes. The lysis in this assay is measured at 700 nm.

Sera from all six mice were also subjected to the alternative pathway dependent hemolysis assay. In this assay, fixed number of rabbit erythrocytes were incubated with 10% normal human serum in Buffer that allows only alternative pathway to be activated. The cellular mixture was incubated with various mice sera and incubated at 37° C. A progressive decrease in light scatter (due to lysis of intact cells) was measured at 700 nm as a function of time in a temperature-controlled ELISA plate reader. The data were recorded and analyzed with a SpectraMax plate reader and SoftMax pro software. As shown in FIG. 10, Mouse A3 demonstrated near complete inhibition with the 1:10 diluted sera. The same mouse demonstrated a good titer in FIG. 9. These two data sets combined together suggest the selection of mouse A3 for further cloning and hybridoma production.

Figure 11:
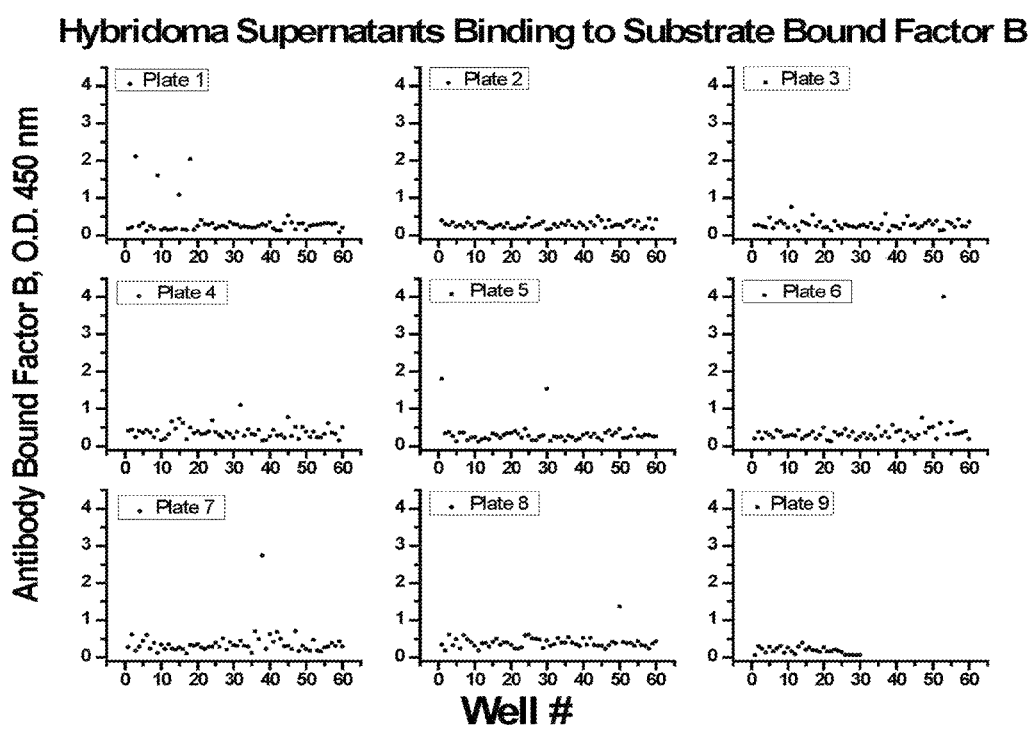
FIG. 11 illustrates the screening of Hybridoma Supernatants for Factor B binding. Spleen from the selected mouse were removed and subjected to cloning to identify a clone that inhibits AP activation. These clones were assayed for binding to substrate-bound human factor B. In a typical setting, the supernatants from various clones were incubated onto Factor B coated wells. The monoclonal antibodies binding to Factor B were detected with an HRP-conjugated goat anti-mouse secondary antibody. Clones that demonstrated an O.D. of one or greater were selected as positives.

The spleen from the selected mouse was removed and fused with the myeloma cells to generate hybridoma. To generate clonal line, the hybridoma cells were distributed in 9 plates with 60 wells in each to allow each well to contain one cell each. These cells were allowed to grow in under appropriate culture conditions. The media was collected and evaluated for factor B binding using factor B coated plates. As shown in FIG. 11, only few clones demonstrated factor B binding.

Figure 12:
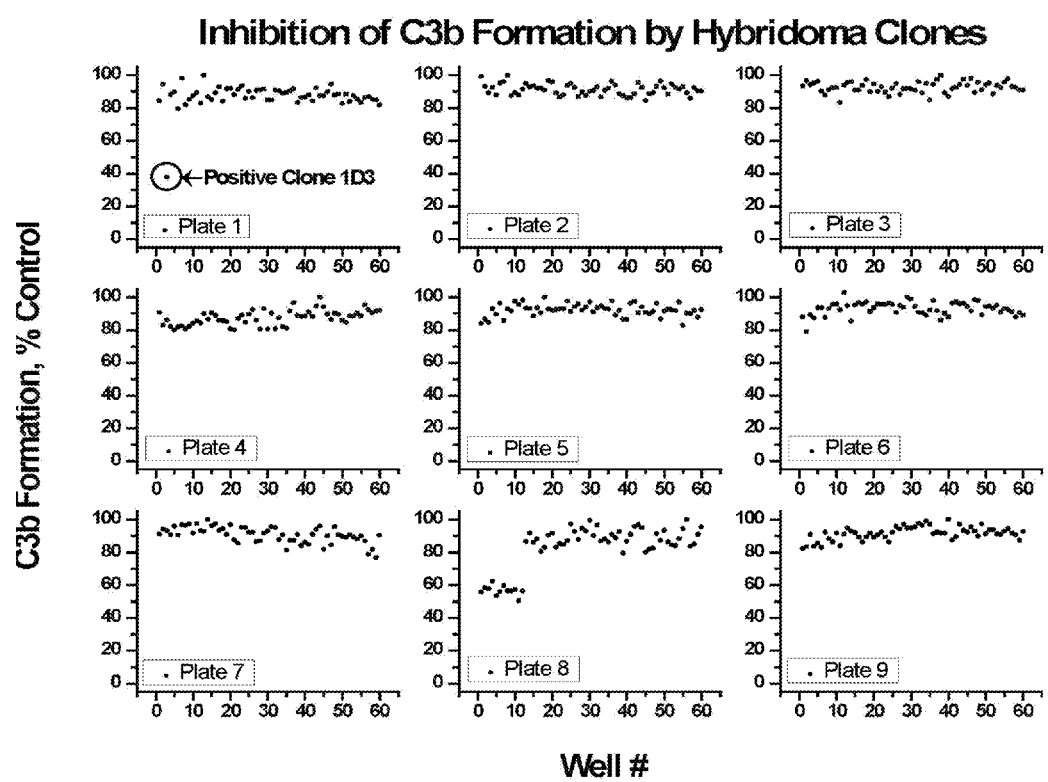
FIG. 12 illustrates the screening of hybridoma clones for inhibition of AP activation via C3b formation: All clones screened in FIG. 11 were subjected to an AP dependent C3b formation assay. Supernatants from clones shown in FIG. 11 were mixed with 10% human serum (final concentration in the mixture) in AP buffer and incubated onto wells immobilized with LPS at 37° C. As a result, LPS will activate AP in human serum and causes C3b deposition. The absence of C3b deposition was taken as a direct measure of AP inhibition. Only one clone, named 1D3 was found to inhibit AP activation. This clone was subcloned several times to identify a single cell population. The final clone was also named as 1D3.
Figure 13:
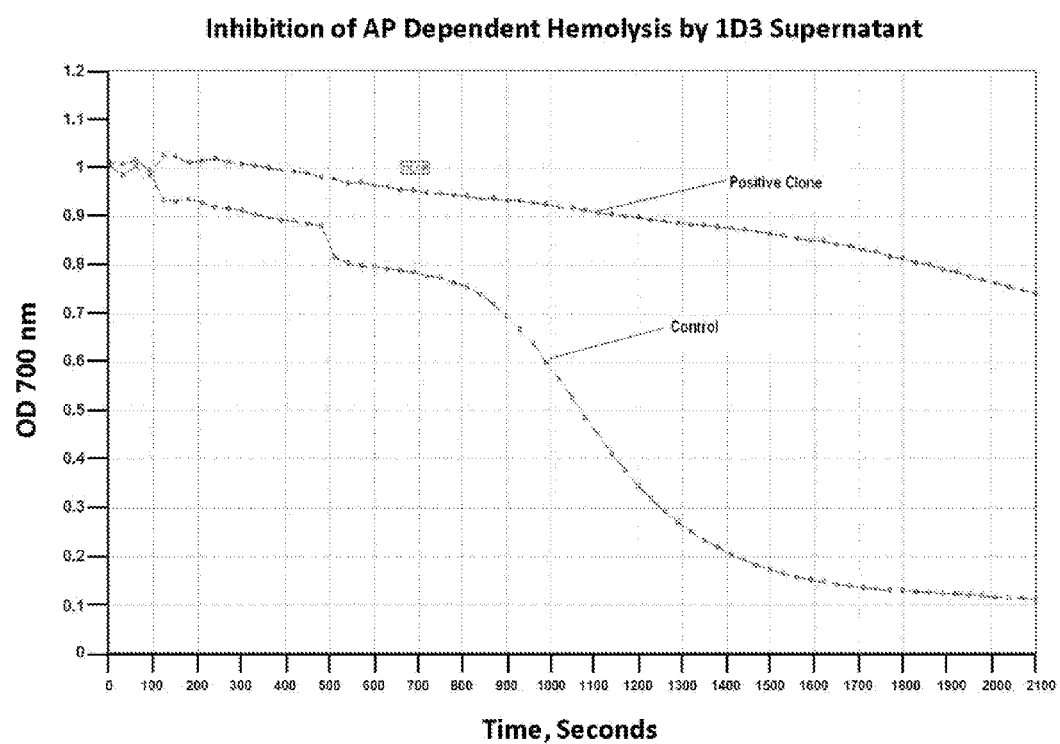
FIG. 13 illustrates the inhibition of AP dependent hemolysis by 1D3 supernatant: 1D3 was also evaluated for AP inhibition using the previously described hemolysis assay. As shown, 1D3 supernatant clearly inhibited hemolysis compared to the serum control. This clone was used to generate anti-Bb specific monoclonal antibodies. The cell line was deposited with ATCC under patent number PTA-8543

Factor B positive clones were then evaluated in a C3b generation assay. In this assay, microtiter wells were coated with LPS (2 µg/50 µl per well) in PBS overnight at 4° C. Uncoated wells served as background controls. After aspirating the LPS solution, wells were treated with blocking solution and incubated with a fixed concentration of normal human serum with and without hybridoma supernatant in AP buffer (Gelatin Veronal Buffer with 5 mM MgCl2, Complement Technologies). Following a 2-h incubation at 37° C., deposited C3b was detected with mouse anti-human C3b antibody (Quidel Corporation) using standard ELISA methodologies essentially as described in the Examples above. The effect of the blocking antibody on the C3b formation is shown in FIG. 12. As shown, only a single clone named 1D3 inhibits C3b production. This particular clone 1D3 was further evaluated in rRBC hemolysis assay and was found to inhibit hemolysis of rRBC in AP buffer as shown in FIG. 13.

Example 3

Production and Purification of 1D3

Figure 14:
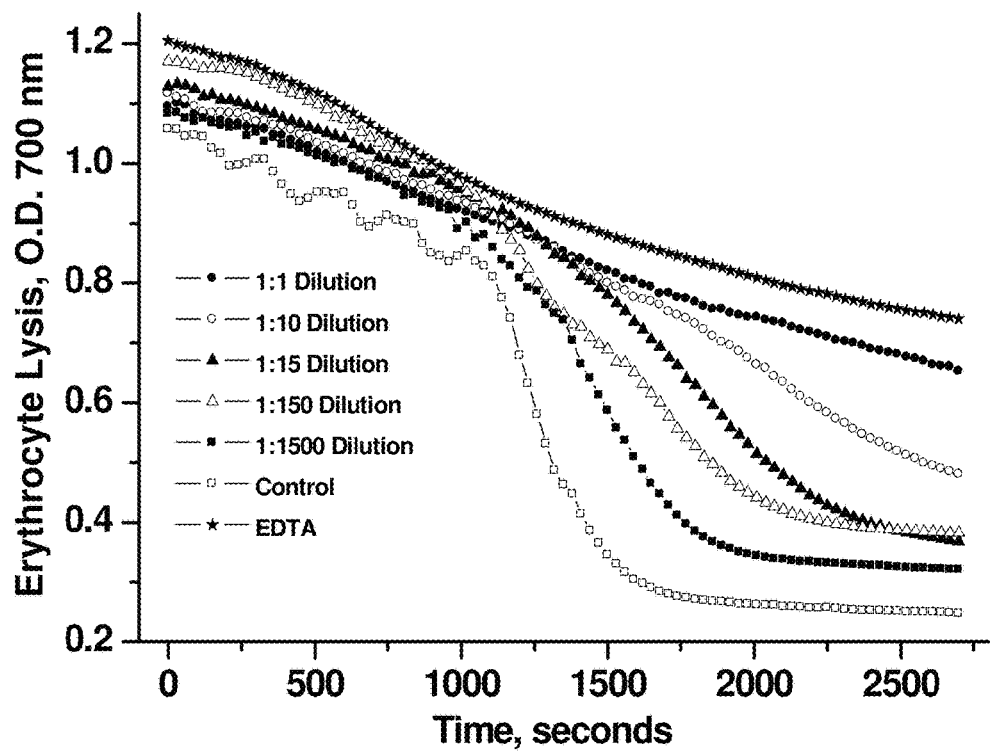
FIG. 14 illustrates inhibition of AP dependent hemolysis by ascites from mouse bearing ID3 cells: The clone 1D3 was injected in mice for bulk production of the monoclonal antibody. Ascites was produced and tested to determine whether the monoclonal antibody in ascites fluid retains its AP inhibitory activity. As shown, ascites fluid was diluted and mixed with rabbit erythrocytes as outlined elsewhere. Crude ascites fluid retains the AP blocking activity.
Figure 15:
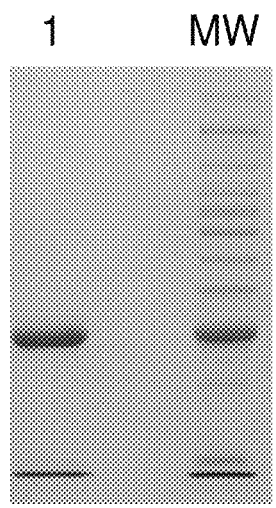
FIG. 15 illustrates SDS-PAGE of the purified monoclonal antibody: The antibody was purified from ascites using standard methods. As shown, the antibody (Lane 1) appears to be free from extraneous proteins.
Figure 16:
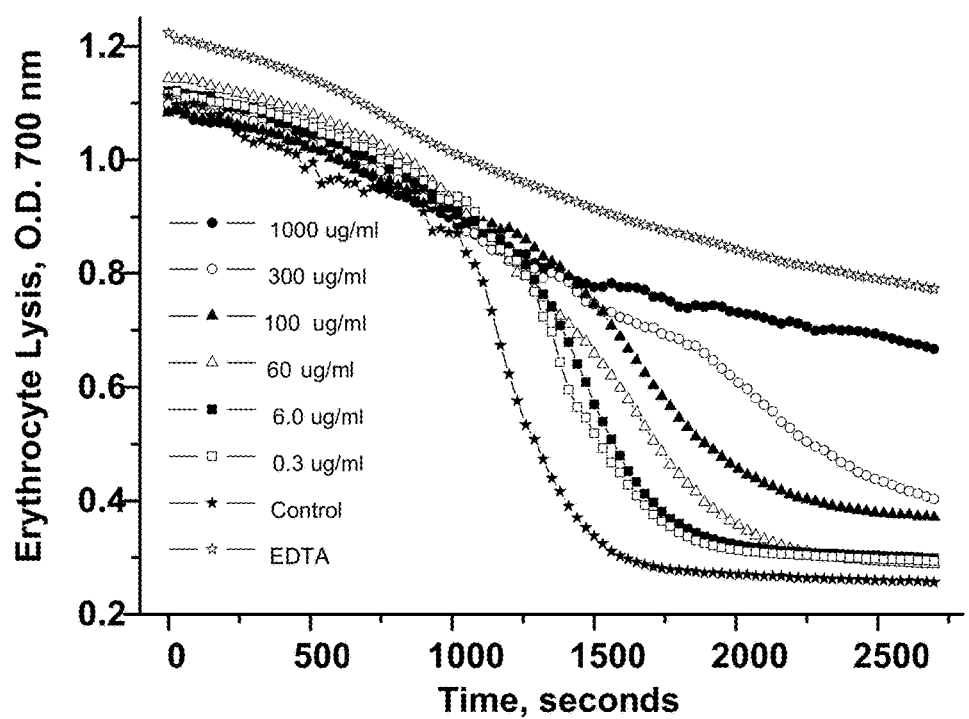
FIG. 16 illustrates inhibition of AP dependent hemolysis by purified monoclonal antibody, named NM001: This monoclonal antibody inhibits hemolysis in a dose dependent manner with nearly 100% inhibition occurring at 100 μg/ml concentration.

1D3 secreting clone was isolated and expanded in culture. To produce large amounts of purified monoclonal antibody, 1D3 cells were injected into mice to produce tumors. The ascites fluid from such tumors were tested for blocking monoclonal antibody activity. As shown in FIG. 14, the monoclonal antibody (NM001) present in ascites fluid blocks hemolysis of rRBC in normal human serum. The blocking monoclonal antibody was purified using protein-G column (purity shown in FIG. 15) and again tested for blocking activity using rRBC as described in Example 1. As shown in FIG. 16, NM001 prevents hemolysis of rRBC at a concentration of 100 ug/ml. NM001 was fragmented into F(ab)2 using Ficin as per previously published methods. The purified fragment was named as Bikaciomab.

Example 4

Binding Affinity of NM001 and Bikaciomab to Factors B

Figure 17:
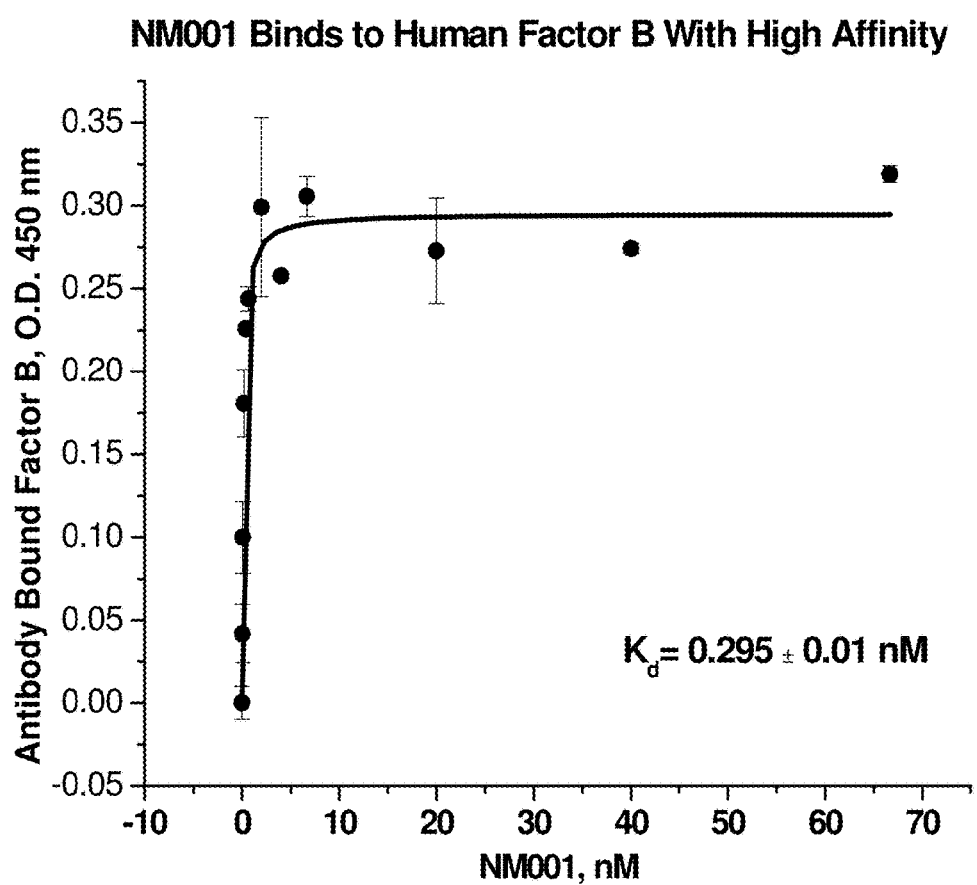
FIG. 17 illustrates NM001 binding to Human Factor B with high affinity: Increasing concentrations of NM001 were incubated in ELISA wells coated with factor B protein. The amount of total binding of NM001 was determined using an HRP-conjugated goat anti-mouse antibody (Sigma). Optical density (O.D.) readings from this assay revealed that NM001 binds factor B with high affinity. Data are presented as the mean O.D.±S.E.M. of triplicate wells of a representative experiment repeated 3 times. In a typical experiment, 12 concentrations of NM001, ranging from 0-70 nM were used. The affinity of binding was found to be in the range of 295 pM.

NM001 binds factor Bb with high affinity. NM001 did not bind the Ba fragment. As shown in FIG. 17, the binding of NM001 to factor B is saturable. FIG. 17 shows high affinity binding of NM001 to Bb fragment. In a typical assay, polystyrene microtiter plates were coated with human factor Bb (2 µg/50 µl per well, (Complement Technologies, San Diego, Calif.) in phosphate buffered saline (PBS) overnight. After aspirating the factor Bb solution, wells were blocked with PBS containing 1% bovine serum albumin (BSA) (Sigma Chemical Company, St. Louis, Mo., Cat. No. A7888)

for 2 hours at room temperature. Wells without factor Bb coating served as background controls. Aliquots of various concentrations of NM001 in blocking solutions were added to factor Bb-coated wells and plates were allowed to sit for 1 hour to allow the monoclonal antibody (NM001) to bind the substrate-bound factor Bb. The plate was rinsed with PBS and factor Bb-bound monoclonal antibody (NM001) was detected by the addition of peroxidase-conjugated goat anti-mouse monoclonal antibody (detection antibody) (Sigma-aldrich, San Diego, Calif.) at 1:2000 dilution in blocking solution, which was allowed to incubate for 1 hour at room temperature. After washing the plates with PBS, 100 µl of 3,3',5,5'-tetramethyl benzidine (TMB) substrate (Kirkegaard & Perry Laboratories, Gaithersburg, Md., Cat. No. A50-65-00) was added. After incubation for 10 minutes at 25° C., the reaction of TMB was quenched by the addition of 100 µl of phosphoric acid, and the plate was read at 450 nm in a microplate reader (e.g., SPECTRA MAX 250, Molecular Devices, Sunnyvale, Calif.).

Figure 24:
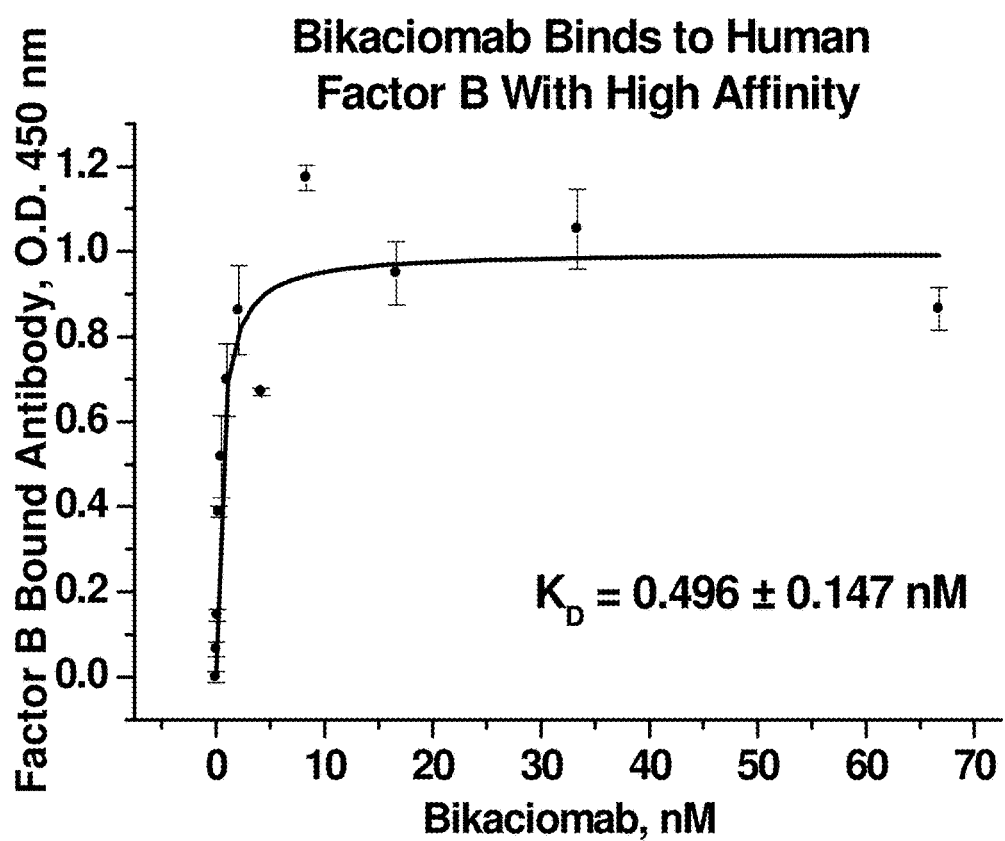
FIG. 24 illustrates BikacioMab binding to human Factor B with high affinity: Bikaciomab is an F(ab')2 fragment of the NM001. Similar to NM001, BikacioMab binds Factor B with high affinity. Various concentrations of BikacioMab were incubated with substrate bound factor B. The bound Factor B was detected with an HRPO-conjugated goat anti-mouse monoclonal antibody. As shown, the affinity of binding is in pM range.

In a separate experiment, we evaluated the binding of Bikaciomab to factor Bb. As shown in FIG. 24, Bikaciomab binds factor Bb with high affinity. Basic methodology for these assays is described in the paragraph above.

Example 5

Evaluation of NM001 and BikacioMab in Alternative Pathway Rabbit Erythrocyte Lysis This cellular assay is based on the formation of terminal complement complex on the surface of the rRBC. As a result, the rRBC are lysed. The evidence of lysed cells is reflected in progressive decrease in light scatter at 700 nm. rRBC are incubated in normal human serum in AP buffer. The surface of rRBC triggers the activation of AP in normal human serum. AP cascade begins and leads to the formation of C5b-9 complex on the surface of the rRBC. Agents that inhibit the activation are expected to inhibit cellular lysis.

Figure 18:
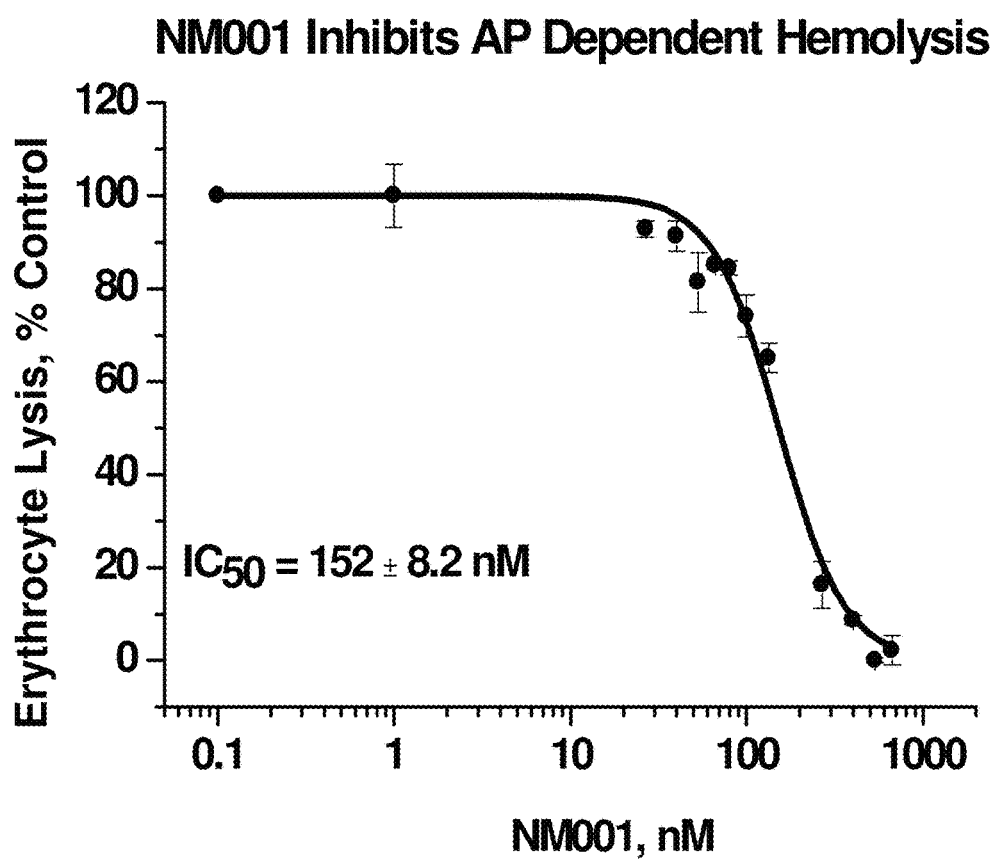
FIG. 18 illustrates that purified NM001 inhibits AP dependent hemolysis: NM001 was tested for its ability to inhibit alternative pathway dependent hemolysis of rabbit erythrocytes in normal human serum in AP buffer. The hemolysis assay was carried out as described elsewhere. At each concentration of NM001 a kinetic curve was generated and the end point readings from each curve were plotted to generate the curve shown here. With this information, the IC50 of NM001's blocking activity was determined. We found that NM001 gave an IC50 of −152 nM.

To evaluate the effect of NM001 on AP activation, various concentrations of NM001 in AP buffer were incubated with normal human serum (10% NHS) at 37° C. with a fixed number of rabbit erythrocytes (Covance) in a temperature controlled ELISA plate reader capable of reading at 700 nm. A progressive decrease in light scatter (due to lysis of intact cells) was measured at 700 nm as a function of time. The data were recorded and analyzed with a SpectraMax 190 plate reader and SoftMax Pro software. Total inhibition was calculated at each concentration of the NM001 and the results were expressed as a % of unlysed controls. Data at each concentration was plotted in a sigmoidal plot with MicroCal Origin Software. FIG. 18 shows that NM001 inhibits AP activation in this cellular assay.

Figure 25:
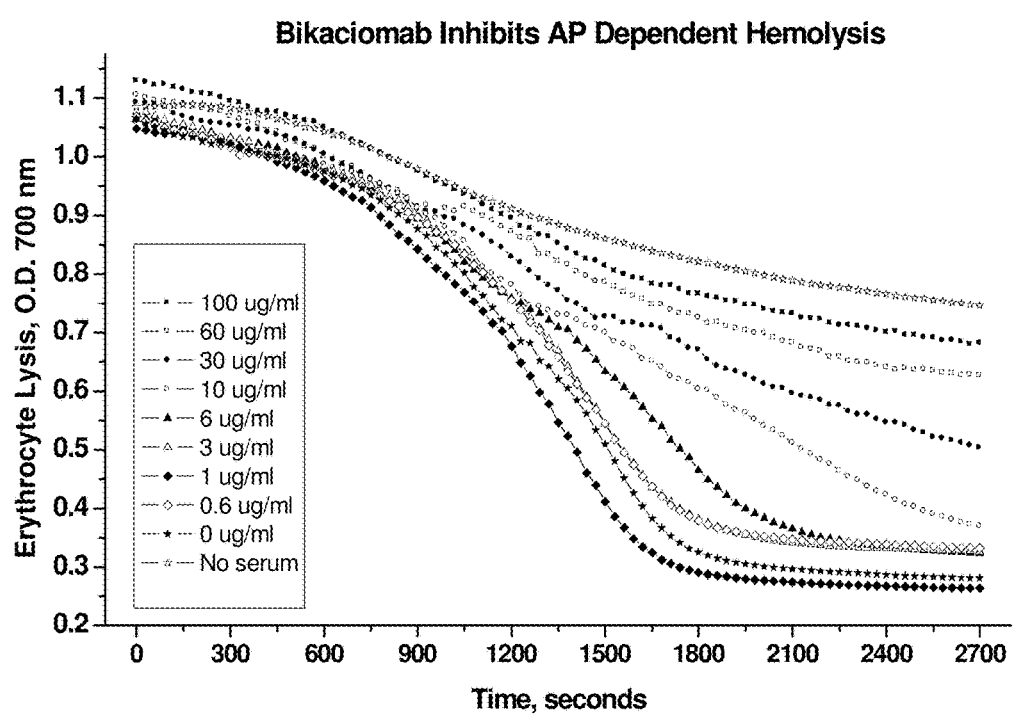
FIG. 25 illustrates BikacioMab inhibition of cellular hemolysis. The assay was conducted as described in FIGS. 10 and 16. Various concentration of Bikaciomab were mixed with normal human serum and incubated with rabbit erythrocytes to allow AP activation to proceed. Bikaciomab inhibited hemolysis of erythrocytes in AP buffer.

FIG. 25 demonstrates the potent activity of BikacioMab in inhibiting erythrocyte lysis. The antibody was able to inhibit lysis in a dose dependent manner. The graph shows that the BikacioMab inhibits lysis in a dose dependent manner.

Example 6

NM001 Does Not Inhibit Factor B Binding to C3b

It has been previously shown that inhibition of factor B binding to C3b is required for inhibition of complement activation. Therefore, antibodies that do not inhibit C3b-B binding are not expected to inhibit AP activation.

Surprisingly, our results demonstrate that NM001 does not inhibit factor B binding to C3b in the presence and absence of properdin. In a typical assay to evaluate the effect of NM001 on factor B binding to C3b, polystyrene microtiter plates were coated with human C3b (0.5 µg/50 µl per well) (Calbiochem, San Diego, Calif., Cat. No. 204860) in phosphate buffered saline (PBS) overnight at 4 degree. After aspirating the C3b solution, wells were blocked with PBS containing 1% BSA (Sigma Chemical Company, St. Louis, Mo., Cat. No. A7888) for 2 hours at room temperature. Wells without C3b coating served as background controls. Aliquots of human factor B (Complement Technologies, Tyler, Tx) at a fixed concentration (100 nM) in blocking solution (containing 5 mM MgCl2) were added to the wells in the presence and absence of variable concentration of NM001. Following 2 hour incubation at room temperature, the wells were extensively rinsed with PBS and C3b-bound factor B was detected by the addition of goat anti-human factor B polyclonal antibody at 1:5000 dilution in blocking solution, which was allowed to incubate for 1 hour at room temperature. After washing the plates with PBS, a peroxidase-conjugated rabbit anti-goat antibody (1:5000 dilution in blocking solution) (American Qualex) was added and allowed to incubate for 1 hour. The plate was again rinsed thoroughly with PBS, and 100 ul of 3,3',5,5'-tetramethyl benzidine (TMB) substrate (Kirkegaard & Perry Laboratories, Gaithersburg, Md., Cat. No. A50-65-00) was added. After incubation for 10 minutes at 25° C., the reaction of TMB was quenched by the addition of 100 µl of phosphoric acid, and the plate was read at 450 nm in a microplate reader (e.g., SPECTRA MAX 250, Molecular Devices, Sunnyvale, Calif.).

Figure 19:
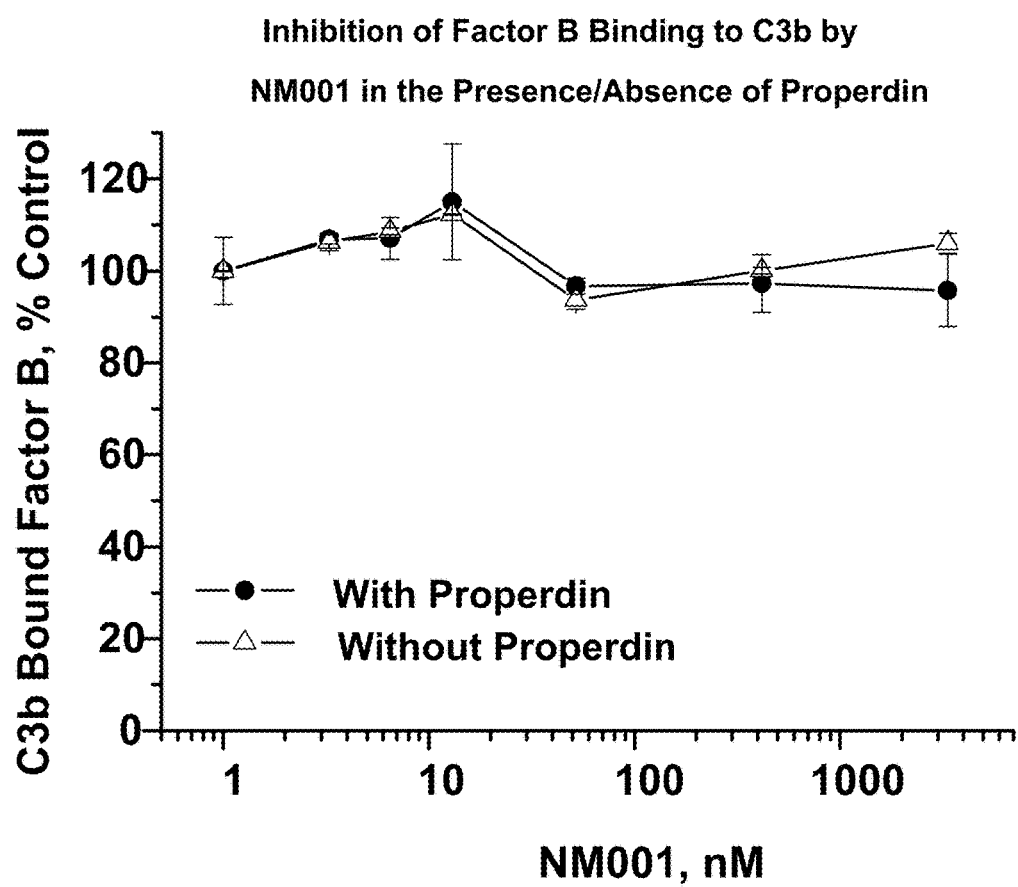
FIG. 19 illustrates the lack of inhibition of inhibition of Factor B binding to C3b or PC3b by NM001 in AP buffer using pure proteins. As shown, NM001 at any concentration does not inhibit Factor B binding to C3b in the presence or absence of properdin. Various concentrations of NM001 were incubated with factor B (fixed concentration) with or without properdin. This solution was incubated with C3b coated plates in AP buffer.
Figure 20:
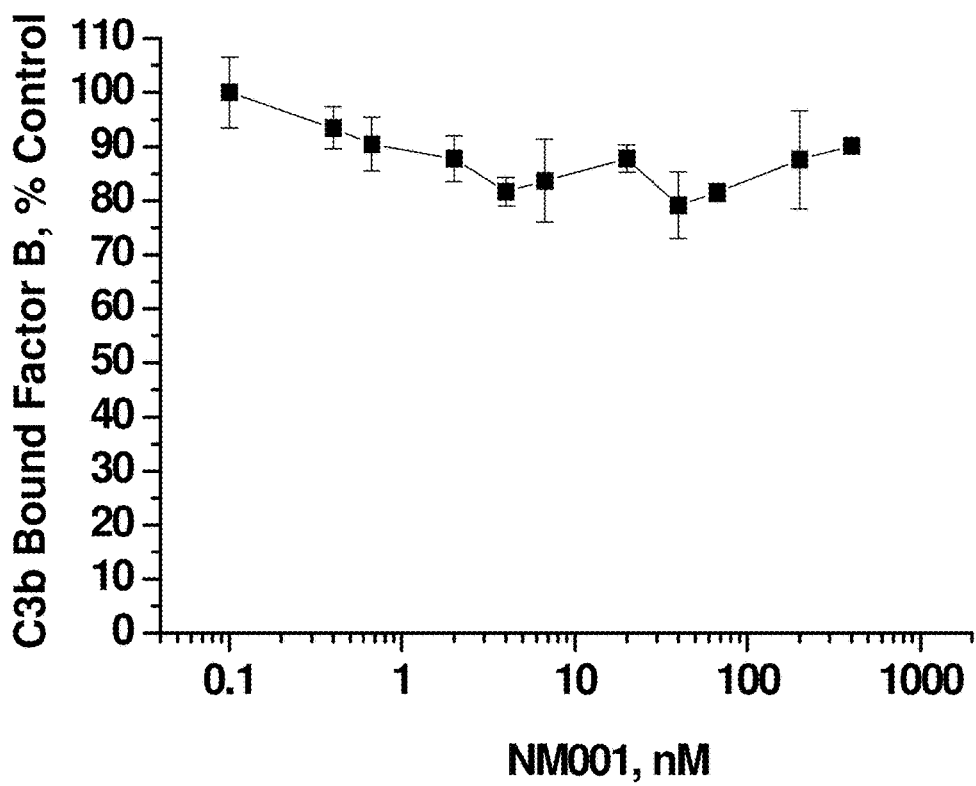
FIG. 20 illustrates the lack of inhibition of Factor B binding to C3b or properdin-bound C3b in AP buffer in normal human serum. Various concentration of NM001 were mixed with diluted human serum and incubated with C3b coated plates. This assay demonstrated that NM001 does not inhibit the binding of factor B to C3b (PC3b).

As shown in FIG. 19, NM001 does not inhibit factor B binding to C3b in the presence and absence of properdin (40 nM). These results were surprising in light of previously known concept where inhibition of factor B binding to C3b was required for complete blockade of complement activation. To confirm these findings factor B solution was replaced with 10% normal human serum and the rest of the experiment was conducted as described in the paragraph above. As shown in FIG. 20, NM001 does not inhibit Factor B binding to C3b. The results shown in FIG. 19 parallel the results shown in FIG. 20 demonstrating that NM001 does not prevent factor B binding to C3b.

Example 7

NM001 and BikacioMab Inhibit C3b Formation

Figure 21:
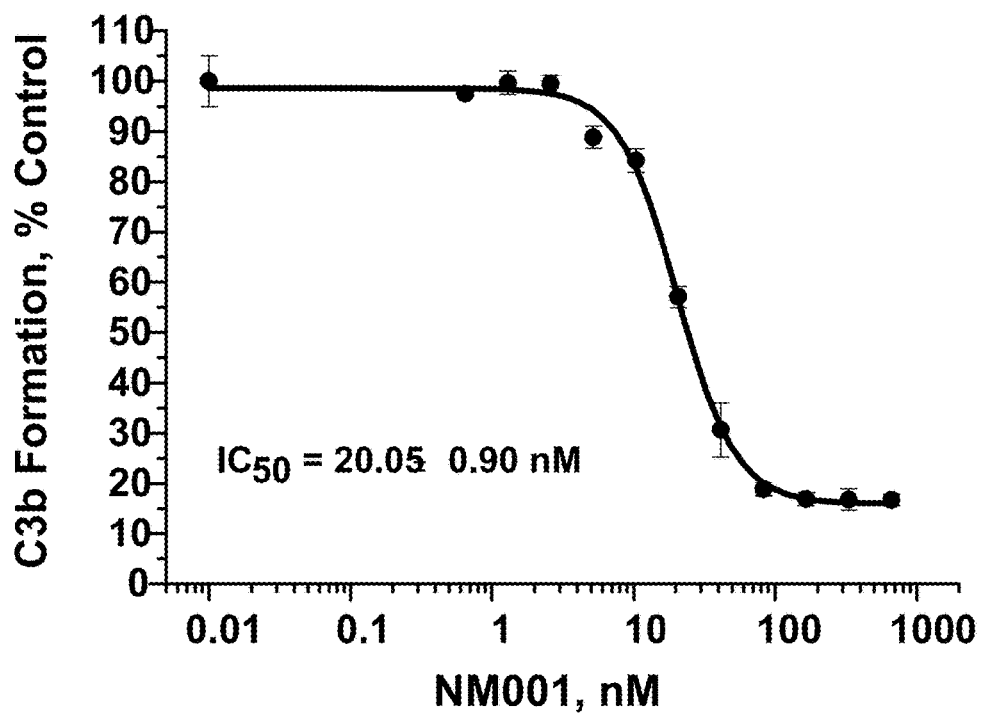
FIG. 21 illustrates that NM001 inhibits formation of C3b via AP. In this assay, Normal human serum with and without NM001 was incubated with substrate-bound LPS. As a result of AP activation C3b is formed. NM001 inhibits C3b formation in a dose dependent manner with an IC50 of around 20 nM.
Figure 27:
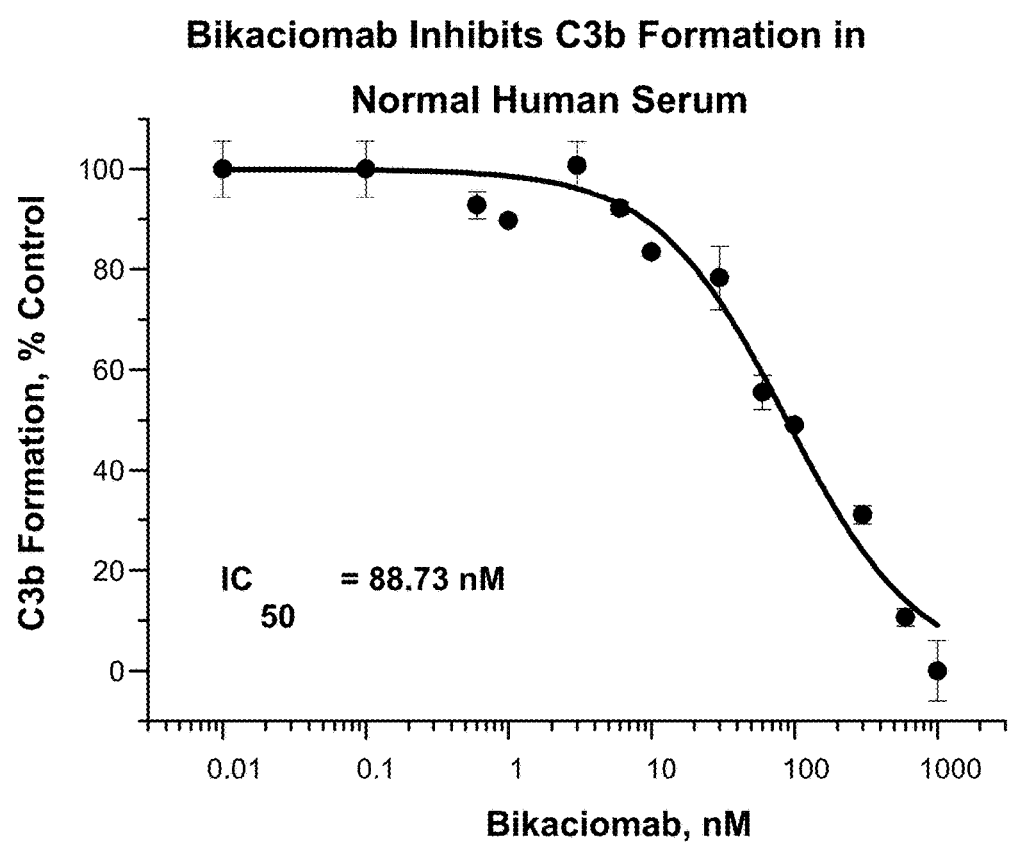
FIG. 27 illustrates Bikaciomab effect on C3b formation in human serum. Similar to FIG. 21, various concentrations of Bikaciomab were added to normal human serum and the mixture incubated on LPS coated plates. LPS stimulates normal human serum and activates the alternative pathway. As a result, C3 convertase is formed which cleaves additional C3 molecules to produce C3b. As shown, BikacioMab inhibits C3b formation in a dose dependent manner with complete inhibition occurring around 80 nM concentration.

The binding data above reveal that NM001 and BikacioMab do not prevent the binding of factor B to C3b. Since factor B is the critical component of the C3 convertase, it was of interest to us to determine whether the lack of factor B binding to C3b might appreciably affect the formation of additional C3b molecules for the amplification of the AP activation. To analyze the effects of the factor B antibody on C3b formation via the alternative pathway, an assay was utilized in which bacterial LPS was used as a substrate to initiate the alternative complement pathway cascade. Previous studies have demonstrated that lipopolysaccharide (LPS) from *Salmonella typhosa* (*S. Typhosa*) (Sigma Chemical Company, Cat. No. 6386) serves as a potent substrate for complement alternative pathway activation. Microtiter wells were coated with LPS (2 µg/50 µlk per well) in PBS overnight at 4° C. Uncoated wells served as background controls. After aspirating the LPS solution, wells were treated with blocking solution and incubated with 10% concentrations of normal human serum containing various concentrations of NM001 (FIG. 21) or Bikaciomab (FIG. 27). Following a 2 hour incubation at 37° C., deposited C3b was detected with mouse anti-human soluble C3c monoclonal antibody (Quidel, SanDiego, Calif.) using standard ELISA methodologies essentially as described in the Examples above. Both FIGS. 21 and 27 demonstrate that the monoclonal antibody NM001 is capable of inhibiting the C3b formation without inhibiting the formation of C3b binding to factor B.

Figure 23:
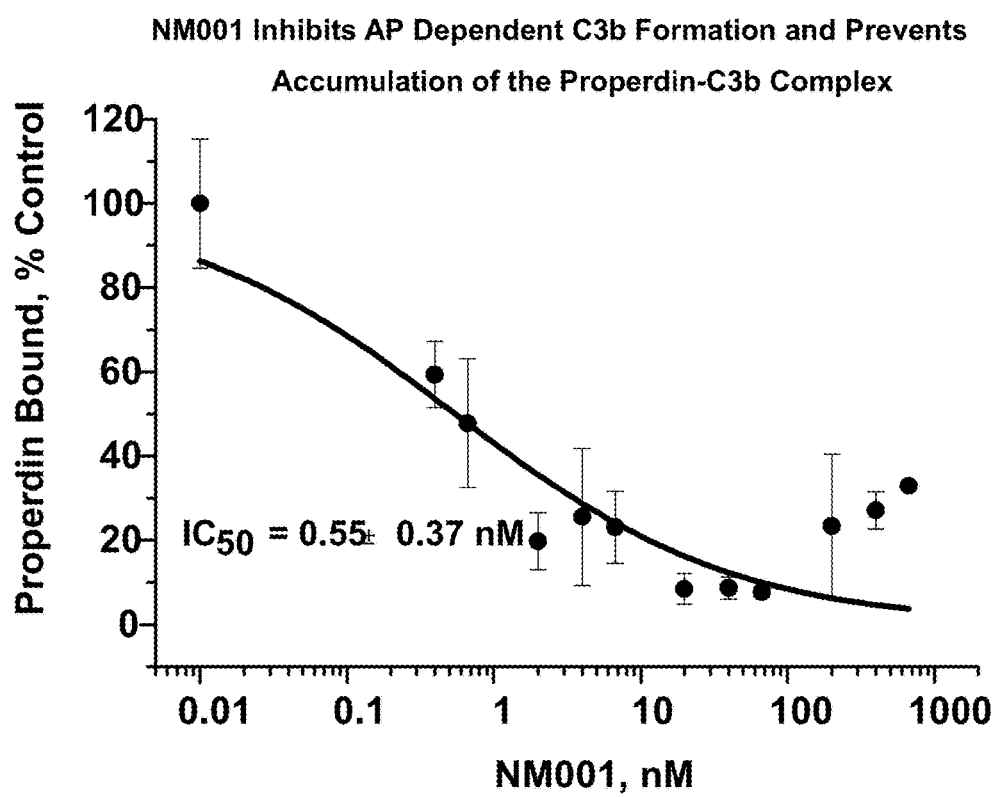
FIG. 23 illustrates NM001 inhibition of C3b formation as shown by the loss of properdin deposition. As a result of complement activation in human serum, C3b is formed. The newly formed C3b associates with Factor P to form the oligomeric C3b. Detection of both C3b and properdin by specific antibodies demonstrates that properdin deposition is inhibited. Inhibition of properdin deposition corroborated with C3b deposition. NM001 does not inhibit properdin binding to C3b or properdin binding to Factor B. As shown, NM001 effectively inhibits the formation of PC3b complex. The IC50 of inhibition is in pMolar range.

In a separate assay, we detected properdin using Quidel anti-P#2 antibody and showed that NM001 inhibits properdin deposition. While the antibody does not interfere with the binding of Properdin to C3b, the NM001 prevented C3b deposition that was pre-bound to C3b (FIG. 23).

Example 8

NM001 and Bikaciomab Inhibit C5b-9 Formation

Figure 22:
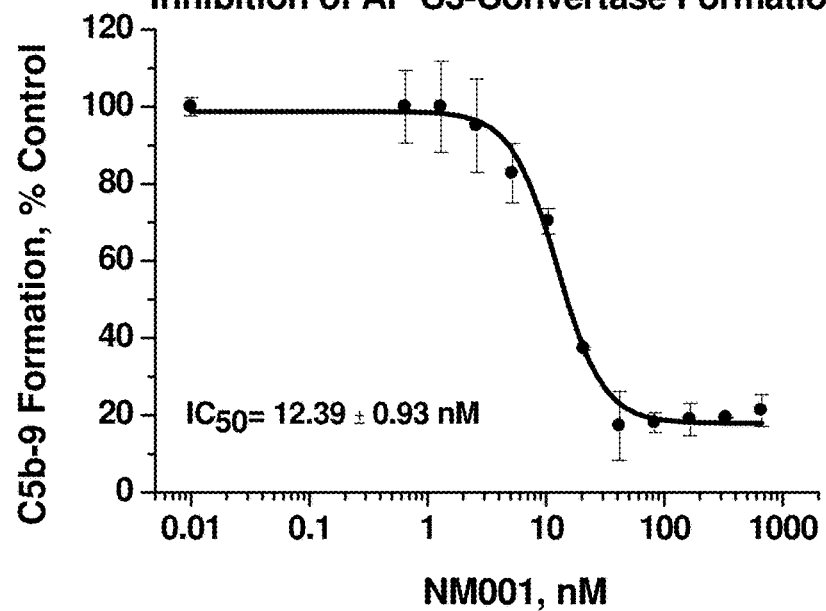
FIG. 22 illustrates that NM001 inhibits C5b-9 formation in human serum. C5b-9 is the terminal component of the complement cascade and is responsible for cellular lysis. Various concentrations of NM001 was added to normal human serum and mixture incubated on LPS coated plates. LPS activates the alternative pathway in human serum. It is expected that inhibition of C3bBb activity by NM001 should inhibit downstream events and therefore should prevent C5b-9 formation. As shown, NM001 inhibits C5b-9 formation in a dose dependent manner with highest inhibition occurring at a 20 nM concentration with an IC50 near 12-13 nM.
Figure 28:
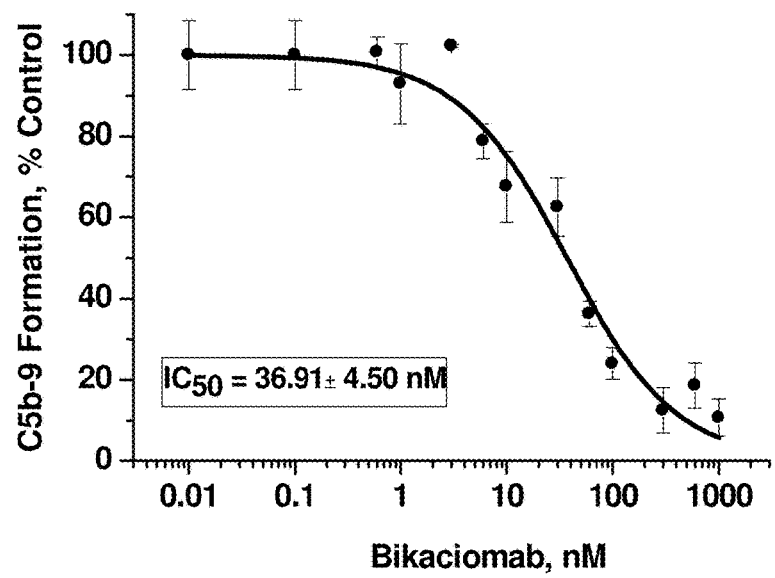
FIG. 28 illustrates Bikaciomab effects on C5b-9 formation in human serum. Similar to the assay described in FIG. 22, BikacioMab inhibits C5b-9 formation in a dose dependent manner with an IC50 of 36 nM. C5b-9 is the terminal component of the complement cascade and is responsible for many deleterious effects when inappropriately activated.

The binding data above reveal that the factor B monoclonal antibody does not prevent the binding of factor B to C3b. Since factor B is the critical component of the C3 convertase, it was of interest to us to determine whether the lack of factor B binding was required for C5b-9 formation because this monoclonal was originally identified using inhibition of C5b-9 in a cellular assay. To analyze the effects of the factor B antibody on C5b-9 formation via the alternative pathway, an assay was utilized in which bacterial LPS was used as a substrate to initiate the alternative complement pathway cascade. Previous studies have demonstrated that lipopolysaccharide (LPS) from *Salmonella typhosa* (*S. Typhosa*) (Sigma Chemical Company, Cat. No. 6386) serves as a potent substrate for complement alternative pathway activation. Microtiter wells were coated with LPS (2 μg/50 μl per well) in PBS overnight at 4 degree. Uncoated wells served as background controls. After aspirating the LPS solution, wells were treated with blocking solution and incubated with 10% concentrations of normal human serum containing various concentrations of NM001 (FIG. 22) or Bikaciomab (FIG. 28). Following a 2 hour incubation at 37° C., deposited C5b-9 was detected with mouse anti-human C5b-9 monoclonal antibody (Quidel, San Diego, Calif.) using standard ELISA methodologies essentially as described in the examples above. Both FIGS. 22 and 28 demonstrate that the anti-Bb is capable of inhibiting the C5b-9 formation without the formation of C3b binding to factor B.

Example 9

BikacioMab Does Not Inhibit the Classical Pathway Activation

The Monoclonal antibody Bb of the present invention does not inhibit the classical pathway. The classical pathway is important for host defense. In this assay, Antibody sensitized sheep erythrocytes is incubated with Normal Human Serum in buffer appropriate for CP activation. The antigen-Antibody complex on the surface of the sheep cells activates the classical complement pathway. As a result erythrocyte lysis occurs. Classical pathway activation occurs in low concentration of serum (1% final). While the knockout mouse data suggests that factor B may participate in classical pathway activation, but our results demonstrate no involvement of the classical pathway.

In a typical assay, erythrocytes are incubated in 1% normal human serum in CP buffer to allow complement activation to occur. As a result of CP activation, C5b-9 is formed on the surface of erythrocytes causing cellular lysis. The progressive decrease in light scattering is measured at 700 nm as a function of time.

Figure 26:
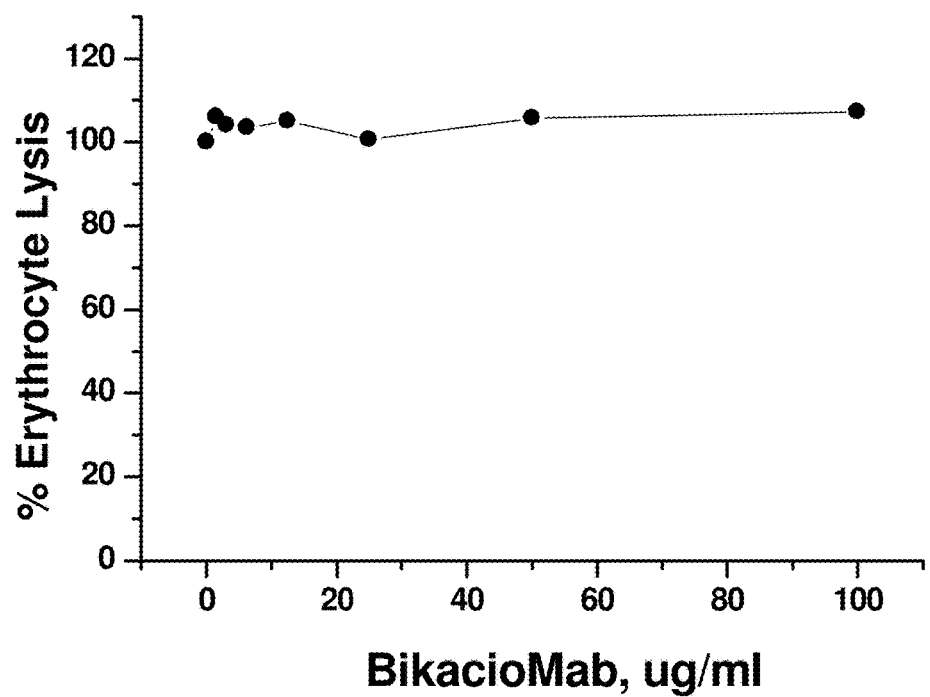
FIG. 26 illustrates that Bikaciomab does not inhibit the classical pathway activity in Gelatin Veronal Buffer that allows activation of both complement pathways. Normal human serum at 1% was incubated with antibody sensitized sheep cells to allo CP activation to occur under test conditions. Control samples without the BikacioMab addition completely lysed the cells. EDTA controls prevented the Lysis. BikacioMab does not inhibit CP mediated cellular lysis in concentration range of 1-100 μg/ml in 1% human serum. The end points following the kinetic analyses were plotted to generate the line shown in Fig.

As shown in FIG. 26, Bikaciomab does not inhibit the classical complement pathway activation. These surprising results further suggest that antibodies can be made that inhibit the specifically prevent the AP activation without affecting the classical pathway. Development of monoclonal antibodies of this invention will leave the classical pathway intact for host defense against infection.

Example 10

Efficacy of BikacioMab in a Tubing Loop Model of Cardiopulmonary Bypass

Examples 1 through 9 demonstrate the evaluation of BikacioMab in in vitro in the presence of human serum. In any disease condition, neutrophils, monocytes and platelets orchestrate the inflammatory response and are critical cell types for clinical control. We have not yet showed the data on the cellular activation. We have chosen this simple model of cardiopulmonary bypass to demonstrate that BikacioMab can prevent cellular activation. In order for the anti-Bb to be a viable drug we need to determine if BikacioMab would inhibit the activation of neutrophils, monocytes, and platelets.

It is known that as blood comes in contact with the artificial surfaces of the extracorporeal circuit, there is significant activation of the alternative complement pathway. To test the effect of Bikaciomab (anti-Bb), Whole blood from a healthy donor was collected into a polypropylene tube containing 5 units of heparin per ml of whole blood. The whole blood was diluted 1:1 with plasmalyte and was aliquoted in 2 ml aliquots with and without drug treatments. PVC tubings were filled with 2.0 ml of the heparinized human blood and closed into a loop with a short piece of silicon tubing. Sample and control tubing loops were rotated vertically in a water bath for 2 hours at 37° C. After incubation, blood samples were transferred into 5 ml siliconized eppendorf tubes. The samples were separated into two aliquots; one aliquot was subjected to flow cytometry studies for cellular activation and the other aliquot was centrifuged to separate the plasma for serological markers. To evaluate the effect of BikacioMab on complement and cellular activation, various concentrations of Bikaciomab were mixed with blood prior to the tubing loop rotation. All tubing loops were rotated at 37° C. for 2 hours before cellular and complement activation is measured.

Figure 29:
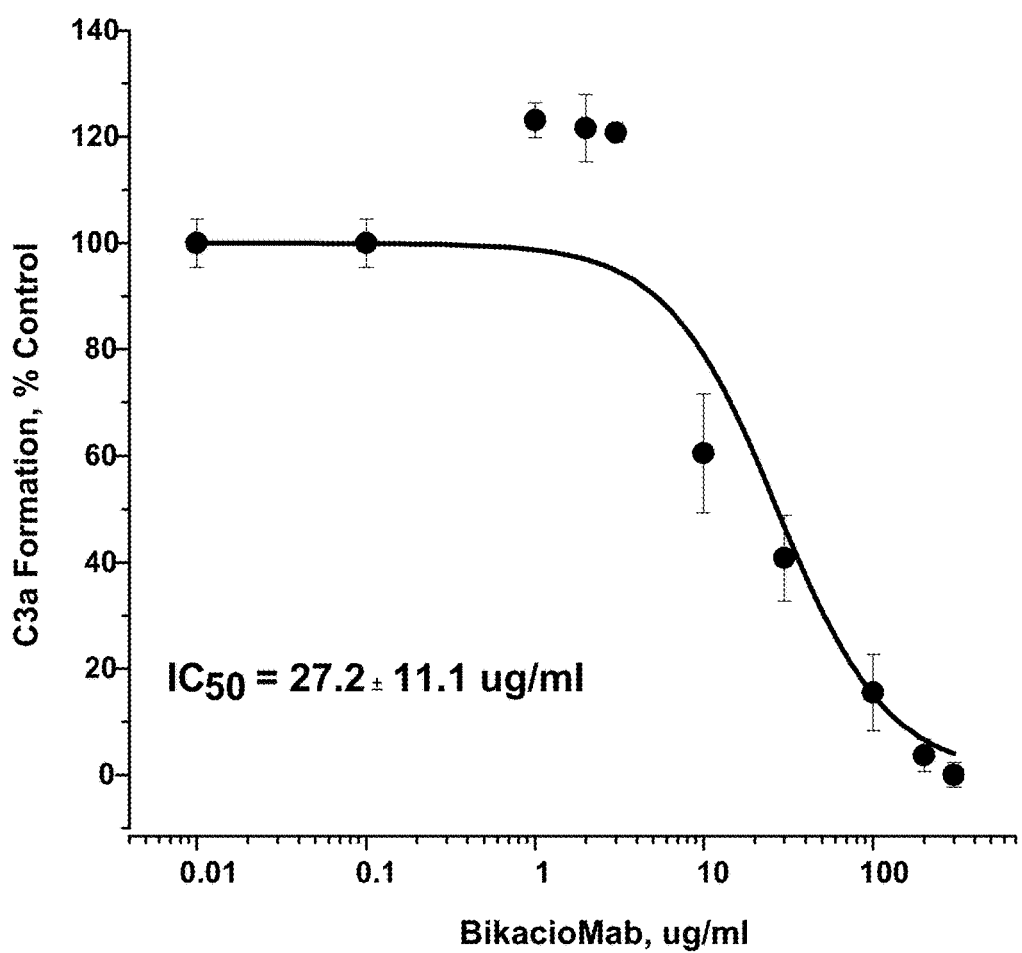
FIG. 29 illustrates that BikacioMab inhibits C3a formation. Various concentrations of BikacioMab were incubated with whole human blood and rotated through the tubing loop. After rotation, the plasma was separated and evaluated for the presence C3a using Quidel's ELISA. BikacioMab inhibits C3a formation in a dose-dependent manner.
Figure 30:
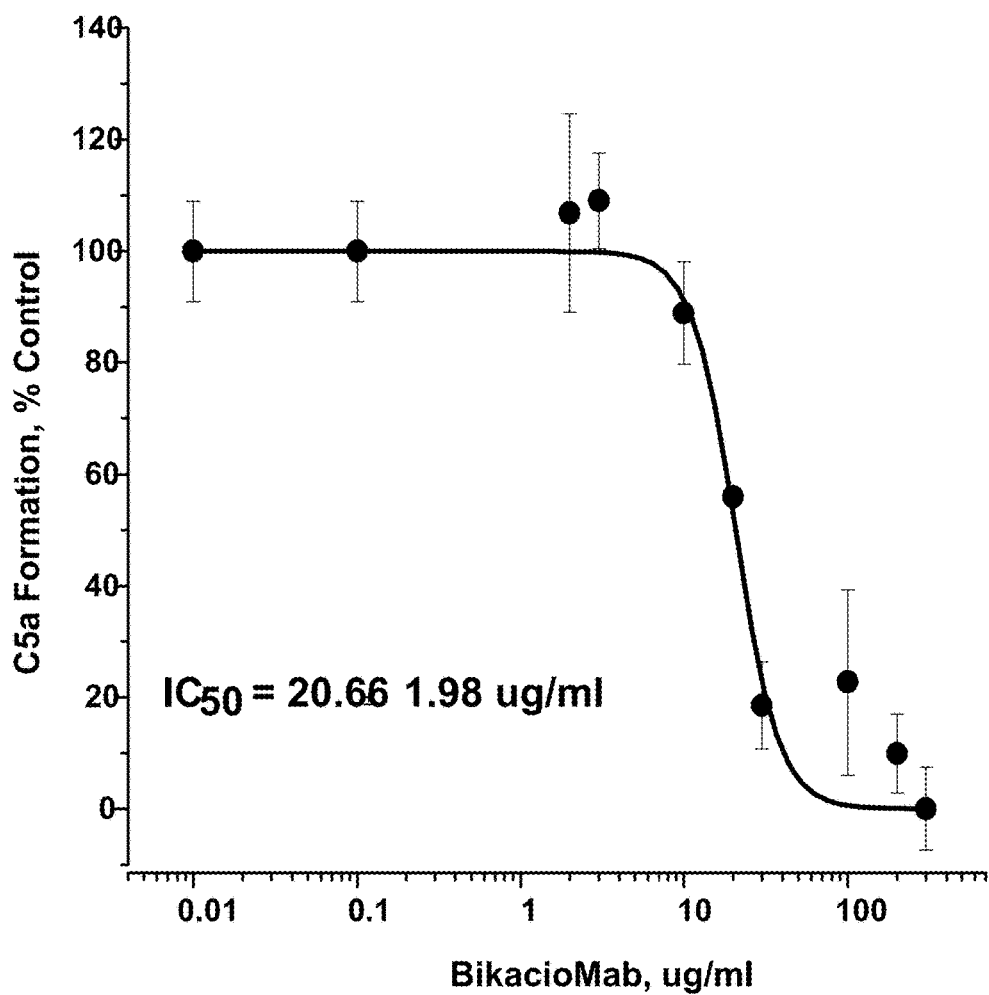
FIG. 30 illustrates that BikacioMab inhibits C5a formation during extracorporeal circulation of whole human blood: The effect of BikacioMab is dose dependent.
Figure 31:
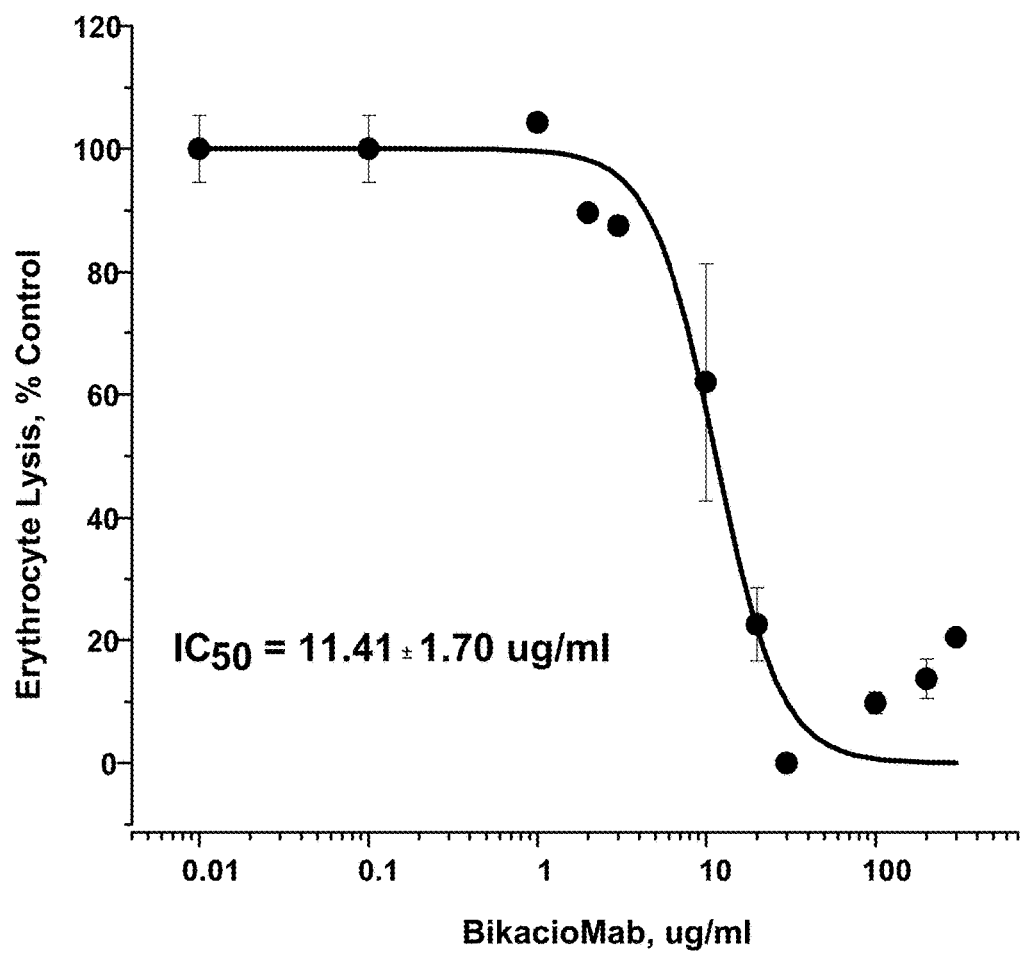
FIG. 31 illustrates BikacioMab, inhibits C5b-9 formation in a dose dependent manner. These data are consistent with the inhibition of C3a, and C5a formation in this model of extra corporeal circulation.

The plasma samples were diluted to 5% with sample diluent buffer and evaluated in a C3a, C5a and sC5b-9 using ELISA assay kits following the manufacturer's instructions (Quidel, Catalog Nos. A015 for C3a and A009 for C5b-9). As shown in FIG. 29, BikacioMab inhibits C3a production in whole blood in a dose dependent manner with complete inhibition occurring at 100 ug/ml of BikacioMab. The $IC_{50}$ of inhibition is in the range of 20 μg/ml. Similar results were obtained with C5a measurements. BikacioMab completely inhibits C5a (FIG. 30) formation and C5b-9 (FIG. 31) formation in a dose dependent manner.

Figure 32:
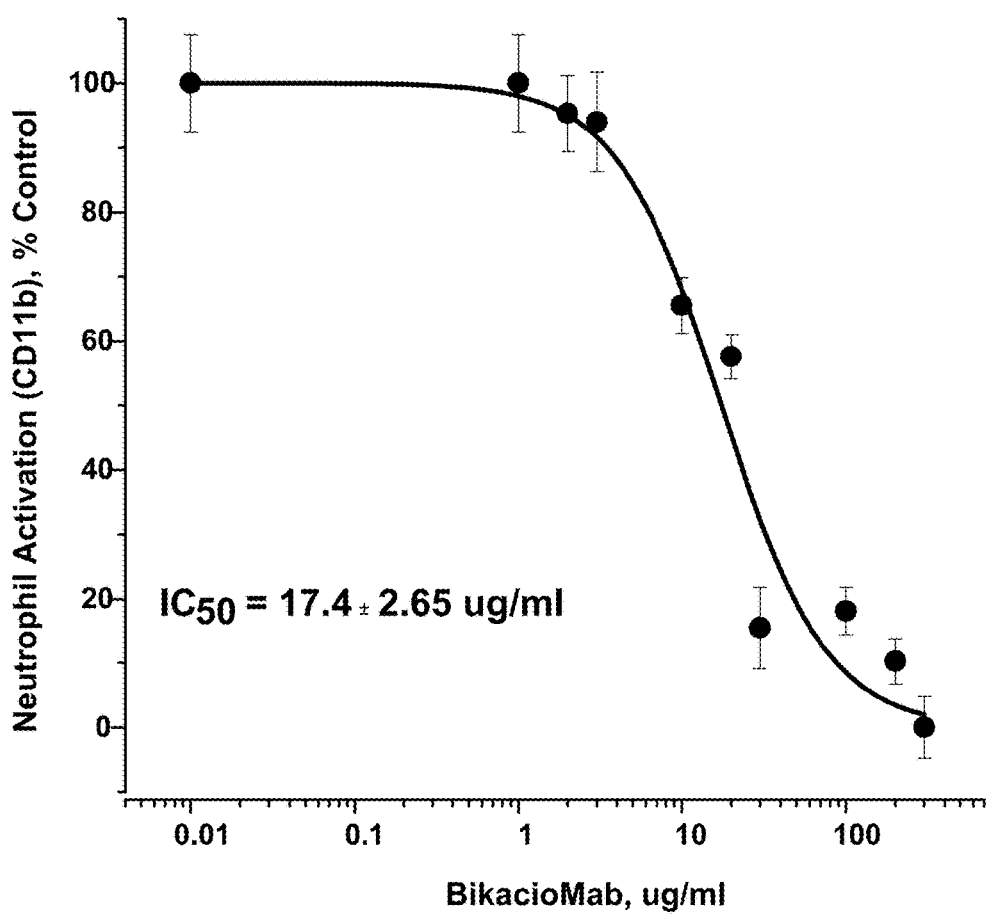
FIG. 32 illustrates Bikaciomab inhibits neutrophil activation. The activation of Neutrophil was measured using flow cytometry approaches. An aliquot of blood sample at each concentration at the end of the 2 h rotation for extracorporeal circulation was stained with FITC-CD15 and PE-CD11b monoclonal antibodies. CD15 is a body marker and CD11b measures expression of CD11b, which is expressed on activated neutrophihls and is a measure of inflammation. As shown, BikacioMab inhibition of CD11b is dose dependent with a complete inhibition occurring at 100 µg/ml concentration.
Figure 33:
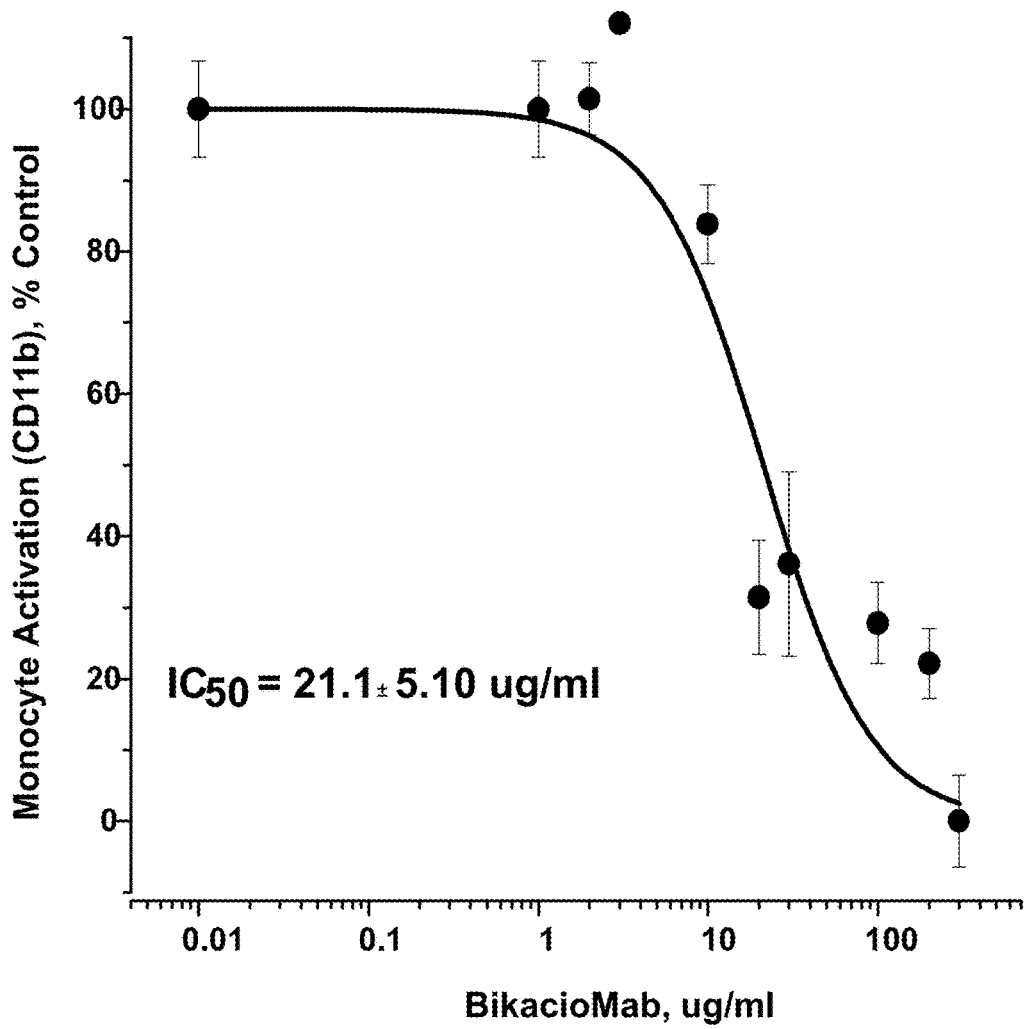
FIG. 33 illustrates BikacioMab inhibits Monocyte activation. Activated monocytes also express CD11b upon activation. The body marker is different than what was used for neutrophils. FITC-CD14 labels monocytes. Bikaciomab inhibits monocyte activation in a dose dependent manner with nearly complete inhibition occurring at around 100 µg/ml in whole blood.
Figure 34:
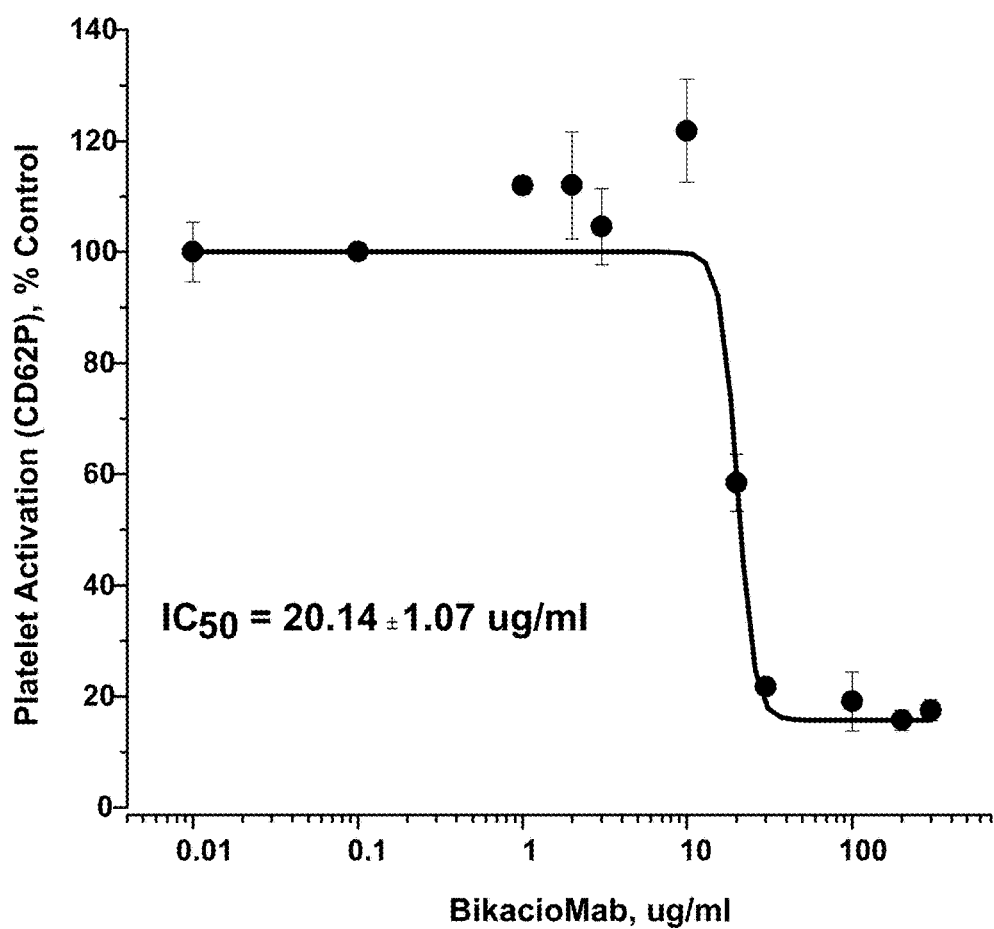
FIG. 34 illustrates BikacioMab inhibits platelet activation. Complete inhibition of platelet activation indicates that the complement is the only mechanism of platelet activation. As shown, nearly 20 µg/ml of BikacioMab completely prevents platelet activation. We measured platelet activation by labeling CD62P with a PE-CD62 antibody. Platelets were identified using CD61 as a bosy marker. Inhibition of cellular activation is consistent with the inhibition of complement activation

Aliquots of blood following the tubing loop were stained with fluorescent labeled antibodies for flow cytomtery studies. Neutrophils were labeled with FITC labeled CD15 and PE labeled CD11b antibodies, monocytes were stained with FITC labeled CD14 and PE labeled CD11b antibodies, and platelets were stained with FITC labeled CD61 and PE labeled CD62P. In a typical method; 20 μl of each of the labeled antibodies were added to the 100 μl of staining buffer containing 50 μl of whole blood. The staining was continued for 20 minutes, following which 2.0 ml of the staining solution was added and the red blood cells were allowed to lyse for 20 minutes. The solution was centrifuged and the cell pellet was washed with PBS and suspended in 0.5 ml of para-formaldehyde solution. The samples were subjected to flow cytometry using CellQuest, BD-LSR I and the data were analyzed using WinList 5.0. Ln Median was used for calculating the shift in CD11b staining for neutrophils and monocytes. % gated dual labeled cells were quantified for platelet populations. FIGS. 32, 33, and 34 show that BikacioMab inhibits neutrophil, monocyte, and platelet activation. Complete inhibition with BikacioMab suggests that the anti-Bb antibody is capable of complete inhibition of cellular activation and that cellular activation is complement dependent.

Figure 35:
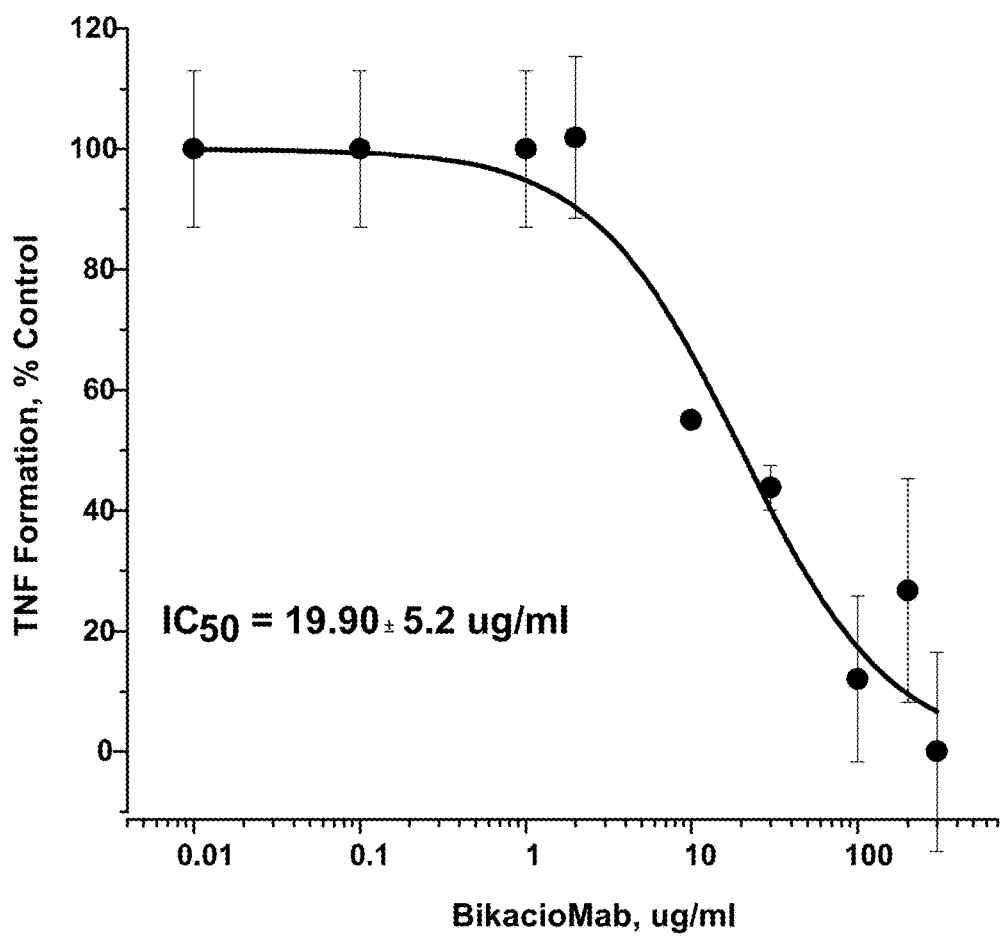
FIG. 35 illustrates Bikaciomab prevents TNF production. Plasma samples following tubing loop were evaluated for TNF using the assay from BD Biosciences.
Figure 36:
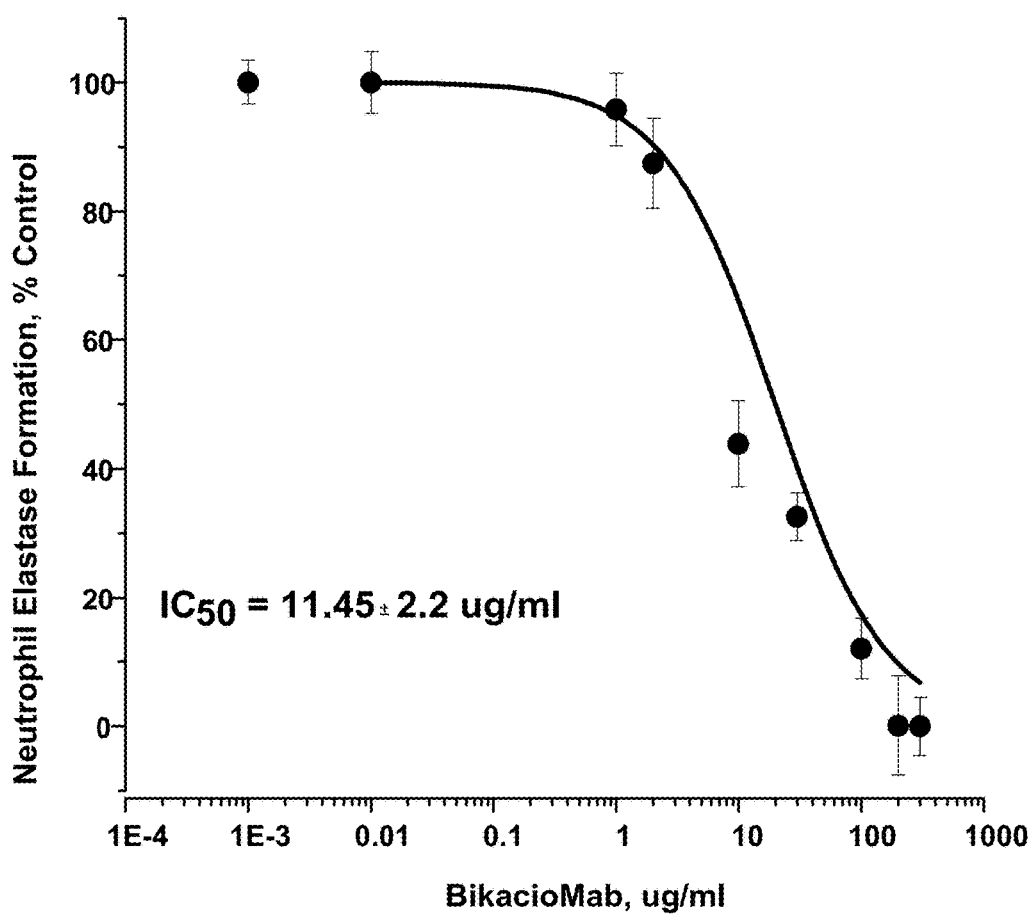
FIG. 36 illustrates Bikaciomab prevents elastase production.

To further demonstrate that Bikaciomab inhibits neutrophil elastase release by neutrophils, aliquots of plasma were also evaluated for neutrophil elastase ELISA developed in-house. In a typical ELISA, anti-elastase antibody was used at 1:500 dilution as a coating antibody. Aliquots of plasma were added to antibody coated wells. The bound elastase-anti-trypsin complex was detected with HRP-conjugated anti-trypsin monoclonal antibody diluted at 1:500 dilution. As shown in FIG. 36 Bikaciomab inhibits elastase release by neutrophils in whole blood. TNF alpha was also measured using BD Kit. The data shown in FIG. 35 shows that Bikaciomab inhibits TNF alpha production. Given the role of TNF in arthritis, the drug anti-Bb can be used in treating several disease indications.

Results

BikacioMab is an F(ab)2 fragment of an anti-Bb monoclonal antibody. The monoclonal antibody is a potent inhibitor of protease activity which binds in the Bb region of factor B. Bikaciomab binds the Bb region with high affinity and inhibits C3a, C5a, and C5b-9 formation. Inhibition of neutrophil, monocyte and platelet activation mirrors the inhibition of complement. Activation of platelet is complement dependent. Bikaciomab totally prevents cellular activation. BikacioMab is characterized as an anti-inflammatory and anti-platelet drug which may be superior to ReoPro. BikacioMab would be an ideal drug for all those clinical indications where alternative complement pathway plays a role in disease pathology.

Example 11

If two antibodies compete with each other for antigen binding, it is understood by those skilled in the art that the two antibodies are binding the same epitope. If the competitive inhibition is 100% then the epitope shared by the antibodies can be exactly the same or be within 50-70% of the first epitope. If two antibodies compete for binding—it means they bind the same region of the protein and therefore are expected to have the similar properties in vitro, ex vivo and in vivo assays. Thus effects of the antibody are expected to be similar in human subjects. The sequences of amino acids may be different in the binding regions of the two antibodies but if they bind and compete—they are similar by those skilled in the art. This concept of binding competition is traditionally used for identification of new chemical, biochemical, peptide, aptamers, SiRNA, antibodies, and or antigen binding fragments thereof. Any structural variants if competes for binding will be considered as being part of the current invention. Antibody competition assays were conducted to determine competing anytibodies that shared a binding region on Bb.

The present invention discloses an anti-Bb antibody that binds to Bb at a specific site and prevents alternative pathway activation without inhibiting the classical pathway activation with same the nanomolar efficacy in both, the normal human serum and the serum from disease patients. Those skilled in the art are familiar with the antibody specificity to the epitope. Therefore, it is well known that any antibody which competes with the antibody is likely binding to the same epitope. It is also known that if two antibodies bind to the same epitope, they are said to be "competing antibodies" and are expected to offer similar results and clinical outcomes in various in vitro, ex vivo and in vivo applications. Additional antibodies can be screened against such competing antibodies in order to identify antibodies with the same function. The ability of one antibody to inhibit the binding of another antibody to properdin is important for identifying other antibodies which share similar function. Such human monoclonal antibodies can be prepared and isolated by a variety of methods well known in the art. Since an antibody's binding to its epitope (or antigen) is dependent on the CDR region/variable regions of the antibody, fragments of the antibody can be used in place of the whole antibody.

Binding of biotinylated NM001 was inhibited by unlabeled NM001 (FIG. 37) in a dose dependent manner. These data suggest that despite having higher binding affinity of NM001 to Bb, NM001 inhibits biotinylated NM001 binding to Bb. Thus antibodies that inhibit binding of NM001 are covered under this invention.

Biotinylated NM1209 binds Bb with the similar strength of affinity as that of NM001 binding to Bb. The binding of NM001 to Bb is not inhibited by NM1209. (FIG. 38) This lack of inhibition by NM1209 (FIG. 38) suggests that even though the affinities of NM001 and NM1209 are substantially similar, the function of these antibodies is not the same. Moreover, if NM001 binding to Bb is not inhibited by these antibodies, it must bind to an entirely different region of Bb. Thus competition binding experiment is important for identifying antibodies that block function.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. A pharmaceutical composition comprising: an isolated anti-Bb antibody or antigen binding portion thereof comprising the heavy chain and light chain CDRs of an antibody produced by a hybridoma cell line deposited under ATCC Accession Number PTA-8543 and a pharmaceutically acceptable carrier.

2. The pharmaceutical composition of claim 1, wherein the antibody is monoclonal.

3. The pharmaceutical composition of claim 1, wherein the antibody is chimeric, recombinant, humanized, or de-immunized.

4. The pharmaceutical composition of claim 1, wherein the antibody is a single chain antibody, IgG, F(ab)$_2$, F(ab')$_2$, F(ab), F(ab') fragment, or truncated antibody.

5. The pharmaceutical composition of claim 1, wherein the antibody or antigen binding portion thereof does not inhibit Factor B and Bb binding to C3b/PC3b in human serum, inhibits C3b formation in human serum, and inhibits formation of C5b-9 in human serum.

6. The pharmaceutical composition of claim 1, being formulated for in vivo or ex vivo administration.

7. A method comprising:
administering to a subject a pharmaceutical composition comprising an isolated anti-Bb antibody or antigen binding portion thereof comprising the heavy and light chain CDRs of an antibody produced by a hybridoma cell line deposited under ATCC Accession Number PTA-8543; and a pharmaceutically acceptable carrier.

8. The method of claim 7, wherein the antibody is monoclonal.

9. The method of claim 7, wherein the antibody is chimeric, recombinant, humanized, or de-immunized.

10. The method of claim 7, wherein the antibody is a single chain antibody, IgG, F(ab)$_2$, F(ab')$_2$, F(ab), F(ab') fragment, or truncated antibody.

11. The method of claim 7, wherein the antibody or antigen binding portion thereof does not inhibit Factor B and Bb binding to C3b/PC3b in human serum, inhibits C3b formation in human serum, and inhibits formation of C5b-9 in human serum.

12. The method of claim 7, wherein the pharmaceutical composition is formulated for in vivo or ex vivo administration.

* * * * *